(12) United States Patent
DeSoutter et al.

(10) Patent No.: US 12,226,136 B2
(45) Date of Patent: Feb. 18, 2025

(54) SURGICAL GUIDE PRODUCTION APPARATUS FOR USE IN A STERILE ENVIRONMENT

(71) Applicant: Prometheus Surgical Limited, Buckinghamshire (GB)

(72) Inventors: George DeSoutter, Buckinghamshire (GB); William DeSoutter, Buckinghamshire (GB); Christopher Block, Buckinghamshire (GB)

(73) Assignee: Prometheus Surgical Limited, Buckinghamshire (GB)

( * ) Notice: Subject to any disclaimer, the term of this patent is extended or adjusted under 35 U.S.C. 154(b) by 1279 days.

(21) Appl. No.: 16/646,931

(22) PCT Filed: Sep. 12, 2018

(86) PCT No.: PCT/GB2018/052590
§ 371 (c)(1),
(2) Date: Mar. 12, 2020

(87) PCT Pub. No.: WO2019/053424
PCT Pub. Date: Mar. 21, 2019

(65) Prior Publication Data
US 2020/0262018 A1    Aug. 20, 2020

(30) Foreign Application Priority Data

Sep. 12, 2017 (GB) ...................... 1714634

(51) Int. Cl.
*A61B 17/88*  (2006.01)
*A61B 46/10*  (2016.01)
(Continued)

(52) U.S. Cl.
CPC .......... *A61B 17/8863* (2013.01); *A61B 46/10* (2016.02); *B23Q 11/0816* (2013.01);
(Continued)

(58) Field of Classification Search
CPC ............ B23Q 11/0816; B23Q 11/0825; B23Q 11/0891; A61B 46/10; A61B 17/8863
See application file for complete search history.

(56) References Cited

U.S. PATENT DOCUMENTS

| 3,583,821 | A | * | 6/1971 | Shaub | ................ | B23Q 11/0816 |
| | | | | | | 408/72 R |
| 5,653,561 | A | * | 8/1997 | May | ................... | B23Q 11/0046 |
| | | | | | | 408/72 R |

(Continued)

FOREIGN PATENT DOCUMENTS

| CN | 102606097 A | 7/2012 |
| CN | 104411266 A | 3/2015 |

(Continued)

OTHER PUBLICATIONS

Office Action dated Mar. 15, 2023 in connection with Chinese patent application No. 201880072776.0, 11 pages including partial English translation.

(Continued)

*Primary Examiner* — Nicholas W Woodall
(74) *Attorney, Agent, or Firm* — Dorsey & Whitney LLP

(57) ABSTRACT

A surgical guide production apparatus and accessories are provided to simplify the process of using the production apparatus within the surgical environment. A cutting attachment is provided for use on a surgical guide production apparatus. The cutting attachment comprises a cutting element, a connector for connecting the cutting element to a drive mechanism of the surgical guide production apparatus so that the cutting element can be driven by the drive mechanism to modify an impression of a surgical site to produce a surgical guide, and a protective barrier. The protective barrier is configured to be positioned around the cutting element to surround a cutting area to help prevent (Continued)

contaminants from entering or leaving the cutting area during modification of the impression.

8 Claims, 27 Drawing Sheets

(51) Int. Cl.
  *B23Q 11/08*   (2006.01)
  *A61B 17/00*   (2006.01)
  *A61B 17/56*   (2006.01)
  *A61B 34/10*   (2016.01)

(52) U.S. Cl.
  CPC .............................. *B23Q 11/0891* (2013.01); *A61B 2017/00526* (2013.01); *A61B 2017/568* (2013.01); *A61B 2034/108* (2016.02)

(56) References Cited

U.S. PATENT DOCUMENTS

| | | | |
|---|---|---|---|
| 5,765,654 A * | 6/1998 | Burger | B23Q 11/0883 408/72 R |
| 6,716,215 B1 * | 4/2004 | David | A61B 17/1622 433/116 |
| 7,901,164 B2 | 3/2011 | Skradski et al. | |
| 10,098,632 B2 | 10/2018 | Gorek et al. | |
| 10,265,869 B2 | 4/2019 | Lohmeier et al. | |
| 2008/0177200 A1 | 7/2008 | Ikehara et al. | |
| 2009/0029636 A1 | 1/2009 | Fujii et al. | |
| 2013/0244846 A1 * | 9/2013 | Koch | A61C 13/0003 269/16 |
| 2015/0202009 A1 | 7/2015 | Nussbaumer et al. | |

FOREIGN PATENT DOCUMENTS

| | | |
|---|---|---|
| CN | 105916455 A | 8/2016 |
| CN | 106466198 A | 3/2017 |
| CN | 106659492 A | 5/2017 |
| JP | S6122612 U | 2/1986 |
| JP | H10612 A | 1/1998 |
| JP | 2000334636 A | 12/2000 |
| JP | 2005063074 A | 3/2005 |
| JP | 2008272909 A | 11/2008 |
| JP | 2014240020 A | 12/2014 |
| JP | 2017500174 A | 1/2017 |
| JP | 2017512527 A | 5/2017 |
| JP | 2017124193 A | 7/2017 |
| WO | 8702883 A1 | 5/1987 |
| WO | 20030101175 A2 | 12/2003 |
| WO | 2005051240 A1 | 6/2005 |
| WO | 2009061728 A1 | 5/2009 |
| WO | 20150075423 A2 | 5/2015 |
| WO | 2015148925 A1 | 10/2015 |
| WO | 2015148928 A1 | 10/2015 |

OTHER PUBLICATIONS

International Preliminary Report on Patentability dated Mar. 17, 2020 in connection with International Patent Application No. PCT/GB2018/052590, 11 pages.

Office Action dated Sep. 5, 2023 in connection with Japanese patent application No. 2022-186640, 9 pages including partial English translation.

Office Action dated Sep. 6, 2023 in connection with Australian patent application No. 2018332144, 4 pages.

Office Action dated Oct. 19, 2022 in connection with Chinse patent application No. 201880072776.0, 11 pages including English translation.

United Kingdom Intellectual Property Office, "Combined Search and Examination Report for GB Application No. GB1714634.1 mailed Feb. 22, 2018", Foreign Counterpart to U.S. Appl. No. 16/646,931, Feb. 22, 2018, pp. 1-7, Published in: GB.

International Search Authority, "International Search Report for PCT/GB2018/052590 dated Aug. 2, 2019", Foreign Counterpart to U.S. Appl. No. 16/646,931, Aug. 2, 2019, pp. 1-6, Published in: WO.

* cited by examiner

SURGICAL GUIDE PRODUCTION APPARATUS FOR USE IN A STERILE ENVIRONMENT

CROSS-REFERENCE TO RELATED APPLICATIONS

This application claims priority under 37 CFR 3.71 to International Patent application No. PCT/GB2018/052590, filed Sep. 12, 2018, entitled "Surgical Guide Production Apparatus for Use in a Sterile Environment," which in turn claims priority to GB Patent Application No. 1714634.1, filed Sep. 12, 2017, each of which is incorporated by reference herein, in the entirety and for all purposes.

TECHNICAL FIELD

The present disclosure relates to surgical guide production apparatuses, cutting attachments for surgical guide production apparatuses, surgical guide carriers and mouldable material carriers.

BACKGROUND

Surgeons often use surgical guides to ensure that they make incisions in patients in the correct positions. For instance, in osteopathy, surgical guides are common to ensure that surgeons drill into the correct location and along the correct axis. As the anatomy of patients varies, surgical guides often have to be custom made for each surgery for each patient.

Whilst additive manufacturing can be utilised to produce surgical guides based on scans of a patient, these guides often provide a poor fit with the patient. This is because the guides may be designed to conform to the geometry of hard anatomical features, such as bone; however, the surgeon, in practice, may not remove all of the surrounding soft tissue. The remaining soft tissue can therefore cause the surgical guides to fit poorly, thereby reducing the accuracy of the surgical procedure.

To counter the above problems, international application WO 2015/075423 A1 (the entirety of which is hereby incorporated by reference) proposes a method in which an impression of the surgical site is taken during surgery. A surgical guide production apparatus located within the operating theatre can then be used to quickly modify the impression (for instance, by drilling the appropriate guide holes or guide features) so that the surgeon has an accurate surgical guide that fits correctly to the current surgical site.

Whilst the above method provides a fast and effective method of producing a surgical guide, there are problems associated with providing a production apparatus within a sterile environment, such as an operating theatre.

Production apparatuses often utilise drill bits, or other cutting elements, to cut holes or incisions in the impression. This can create debris that can contaminate the surrounding area, including sterilised equipment.

In addition, it is often difficult to sterilise large medical devices with a number of moving parts. The sterilisation procedure means that there is a period of time after a surgery has been completed in which the production apparatus cannot be used. This means that either a similar operation cannot be performed until the production apparatus has been sterilised, or the hospital must purchase additional production apparatuses for use when one is being sterilised.

Furthermore, nurses and surgeons must maintain the sterile areas of the operating theatre during the operation. Whilst certain parts of the production apparatus may be sterilised, other parts may not be sterilised in order to save costs and speed up the sterilisation process. There is therefore a risk that a nurse or doctor using the production apparatus may accidentally touch a non-sterile area. This could lead to the sterile field within the operating theatre being contaminated if the nurse or doctor continues to work without re-sterilising the affected part of the clinician's body or clothing. This could lead to the nurse or doctor having to stop work to replace sterile garments or scrub up again to sterilise contaminated skin.

There is therefore a need for an improved surgical guide production apparatus and associated attachments to help maintain the sterile environment within an operating theatre.

BRIEF DESCRIPTION OF THE DRAWINGS

Embodiments of the present invention are described herein with reference to the accompanying figures, in which.

SUMMARY OF INVENTION

Figure 1:
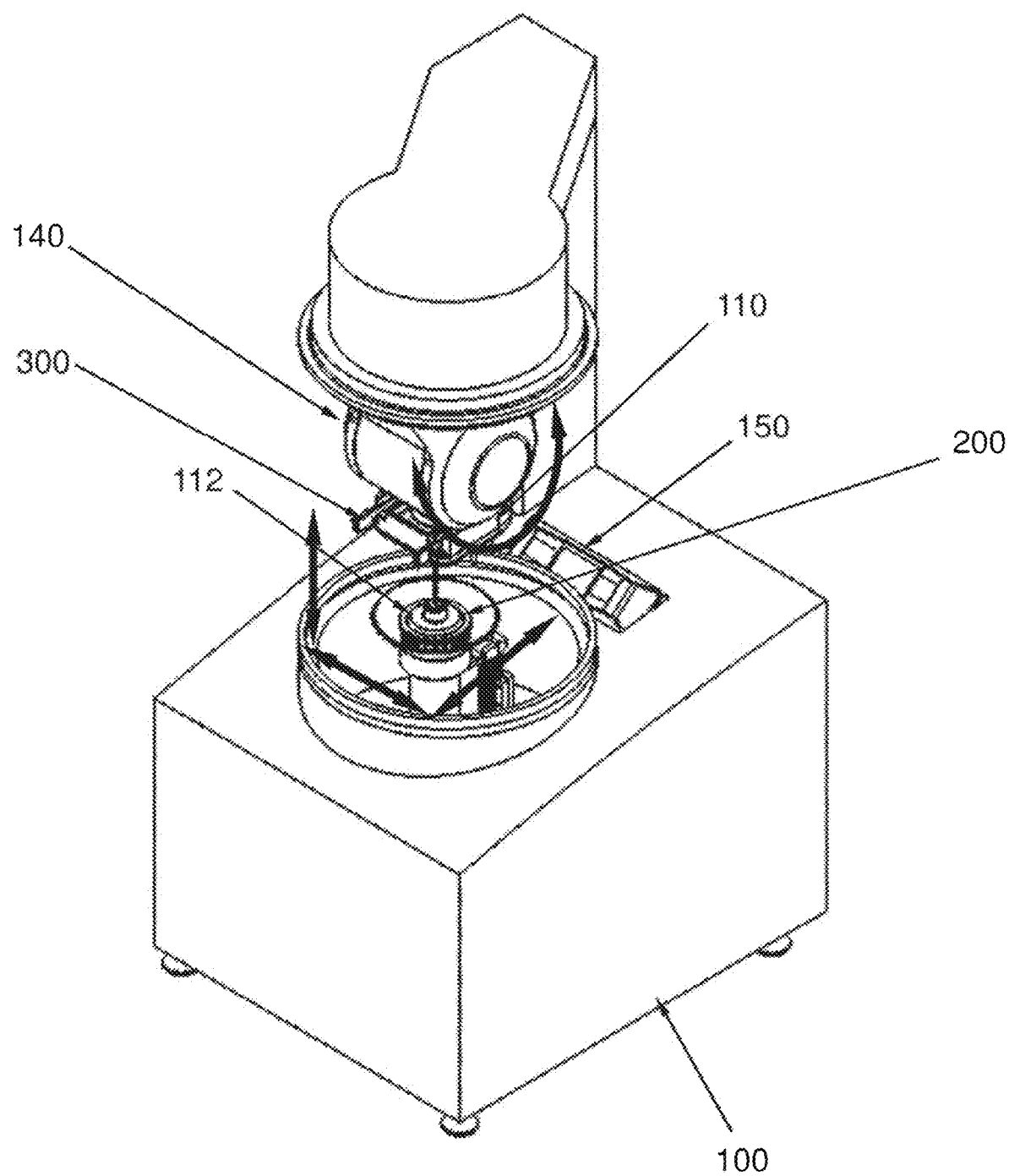
FIG. 1 shows a production apparatus in accordance with an embodiment.

According to a first aspect of the invention there is provided a cutting attachment for use on a surgical guide production apparatus, the cutting attachment comprising: a cutting element; a connector for connecting the cutting element to a drive mechanism of the surgical guide production apparatus so that the cutting element can be driven by the drive mechanism to modify an impression of a surgical site to produce a surgical guide; and a protective barrier configured to be positioned around the cutting element to surround a cutting area to help prevent contaminants from entering or leaving the cutting area during modification of the impression.

By providing a protective barrier integrated into the cutting attachment, the protective barrier can help to shield the sterile parts of the cutting attachment and surgical guide production apparatus to help avoid contamination of the impression of the surgical site during modification.

The protective barrier may be rigid or flexible. If the protective barrier is flexible (e.g. a flexible sheet such as a barrier drape), then the user may grip the cutting attachment with the protective barrier wrapped around the cutting element to help to shield the cutting elements when it is being mounted to the surgical guide production apparatus.

In use, the protective barrier may be positioned around the cutting area, e.g. by raising the protective barrier to surround or enclose the cutting area. The cutting area may include the cutting element, the surgical guide and the local surrounding space. Accordingly, the cutting area may be a volume surrounding the space in which the surgical guide may be modified.

The protective barrier may be connected to the cutting element to form a 360° seal around the cutting element. This ensures that no debris can pass between the protective batter and the cutting element.

Advantageously, the cutting attachment may further comprise a support connected to the protective barrier and configured to be moved to position the protective barrier around the cutting area.

The support may be configured to couple to a driven support arm of the surgical production apparatus so that the surgical production apparatus can move the protective barrier into position around the cutting area.

In addition, the cutting attachment may further comprise a connector for connecting an intermediate part of the protective barrier to a base of the surgical guide production apparatus at the base of the cutting area. Where the protective barrier is a flexible sheet, such as a barrier drape, this can help to ensure that a straight wall is set up at the outskirts of the cutting area and can help to ensure that sufficient slack in the protective barrier is provided at the base to allow the cutting element to be moved by the surgical guide production apparatus.

Advantageously, the protective barrier may comprise a flexible sheet. This allows the cutting element to be moved during modification without compromising the sterile barrier.

Advantageously, the cutting attachment may further comprise one or more support frames connected to the protective barrier and configured to be positioned around the cutting area to prevent the protective barrier from entering the cutting area. Where the protective barrier is a flexible sheet, this can help to prevent the sheet from sagging, billowing, bowing into, or otherwise impinging on the cutting area.

The cutting attachment may comprise a lower support frame configured to weigh down the protective barrier to position at least part of the protective barrier against a base of the production apparatus. Alternatively or in addition, the lower support frame may be configured to couple to the base of the production apparatus.

The cutting element may comprise a cutting element for a power tool. This may be any power tool cutting element, e.g. any tool that may be actuated in a cutting motion by a power tool. This could be a drill bit, a saw, a bur, a reamer, a knife, a needle, or any other appropriate cutting element. Power tools can create a large amount of debris. In this case, the protective barrier serves an additional function of preventing contamination of the surrounding area by debris from the cutting.

Advantageously, the cutting attachment may be sterile or configured to be sterilised. In this embodiment, the cutting attachment should be fabricated from materials that are suitable for sterilisation, either before purchase, or by the end user. This ensures that it may be used within a sterile environment such as an operating theatre.

Advantageously, the cutting attachment may further comprise a coding element indicating a type of the cutting attachment and configured to be read by the surgical guide production apparatus so that the surgical guide production apparatus can verify that the correct type of cutting attachment has been fitted. This helps to prevent errors when producing the surgical guide.

The coding element may be a radio-frequency identification (RFID) chip, a barcode, QR code, memory device (e.g. flash), or any other form of machine-readable media. For instance, the coding element may encode the type of cutting element via its physical shape, which may be read by the production apparatus via, for instance, an optical sensor, or a configuration of buttons. Different types of cutting attachment may include different types of cutting element (e.g. drill, bur, etc.), different lengths or diameters of cutting element, different materials of the cutting element and/or different manufacturers of the cutting attachment.

According to a second aspect of the invention there is provided a surgical guide carrier for attaching to a surgical guide production apparatus, the surgical guide carrier comprising: a connector for mounting the surgical guide carrier to a mount on the surgical guide production apparatus; a coupling portion for receiving and releasably retaining an impression of a surgical site so that, when the impression is retained in the surgical guide carrier, and when the surgical guide carrier is mounted on the surgical guide production apparatus, the surgical guide production apparatus can modify the impression to produce a surgical guide; and a protective barrier configured to be positioned around at least part of the surgical guide production apparatus to provide a barrier between the surgical guide and at least part of the surgical guide production apparatus.

The impression of the surgical site may be taken on a mouldable material carrier that is configured to be coupled to the surgical guide carrier via the coupling portion. By providing the protective barrier, the impression of the surgical site may be protected from sections of the surgical guide production apparatus that may not have been sterilised. This is advantageous, as it can be difficult to sterilise devices with moving parts, and reduces the downtime of the surgical guide production apparatus between operations. The protective barrier also helps to prevent debris from the modification of the impression from contaminating the surgical guide production apparatus.

The protective barrier may be connected to the coupling portion to provide a 360° seal between the protective barrier and the coupling portion. This prevents contaminants from passing between the protective barrier and the coupling portion.

The surgical guide carrier may be configured to be mounted to the production apparatus in a predefined position and orientation and/or may comprise fiducial markers to allow the position and/or orientation of the surgical guide carrier relative to the production apparatus to be determined.

Advantageously, the surgical guide carrier may be sterile, or configured to be sterilised, and the protective barrier may provide a sterile barrier to help prevent contamination of the impression during modification. This ensures that it may be used within a sterile environment such as an operating theatre.

Advantageously, the protective barrier may be flexible. This may be a flexible sheet. This allows the coupling portion to be moved during modification without compromising the sterile barrier.

In one embodiment the surgical guide carrier is configured such that the protective barrier may be secured to the surgical guide production apparatus such that the protective barrier surrounds the mount of the surgical guide production apparatus. This protects the user's hands from possible contamination from the mount when mounting the surgical guide carrier on the surgical guide production apparatus and when mounting or removing the mouldable material carrier. Furthermore, the mount may be located on or include a rotation mechanism to allow the impression to be positioned appropriately for modification. Such mechanisms can be difficult to sterilise. Providing a protective barrier for surrounding the mount (and possibly also the rotation mechanism) therefore avoids the need to sterilise this section of the production apparatus.

The surgical guide carrier may further comprise a support frame connected to the protective barrier, the support frame forming an opening into which the mount of the surgical guide production apparatus may be received, being configured such that the opening may be expanded from a first configuration to a second configuration that is larger than the first configuration so that the support frame can fit over a securing section of the surgical guide production apparatus, and wherein the support frame is biased towards the first configuration so that the support frame, when released, returns to the first configuration to secure the protective barrier over the securing section. This provides a simple mechanism for securing the protective barrier to the production apparatus.

The surgical guide carrier may further comprise one or more levers connected to the support frame and configured to allow the support frame to receive an expanding force to expand the opening from the first configuration to the second configuration. The one or more levers may be integrated into one or more corresponding handles that protrude away from the opening to help keep the user's hands away from the production apparatus when securing the protective barrier to the production apparatus.

Advantageously, the support frame may comprise: one or more locking members, each configured to be urged towards a first position in which the locking member protrudes into the opening, and configured to be movable from the first position to a second position to expand the opening; or, a resilient loop configured to be expandable to expand the opening.

Advantageously, the surgical guide carrier may further comprise a handle connected to the support frame and protruding away from the opening. This helps to position the user's hands away from the production apparatus when attaching the protective barrier to the production apparatus to avoid accidental contamination.

The surgical guide carrier may further comprise a rotatable section upon which the coupling portion is located, the rotatable section being configured to receive a rotating force from the surgical guide production apparatus so that the coupling portion can be rotated into position for production of the surgical guide.

Advantageously, the surgical guide carrier may further comprise a coding element indicating a type of the surgical guide carrier and configured to be read by the surgical guide production apparatus so that the surgical guide production apparatus can verify that the correct type of surgical guide carrier has been fitted. The coding element may be a radio-frequency identification (RFID) chip, a barcode, QR code, memory device (e.g. flash), or any other form of machine-readable media. For instance, the coding element may encode the type of surgical guide carrier via its physical shape, which may be read by the production apparatus via, for instance, an optical sensor, or a configuration of buttons. Different types of surgical guide carrier may include different types of carrier (e.g. for different types of impression/surgical guide), different sizes or shapes of carrier, different materials of the surgical guide carrier and/or different manufacturers of the surgical guide carrier.

According to a third aspect of the invention there is provided a mouldable material carrier for use in producing an impression of a surgical site, the mouldable material carrier comprising a first surface upon which mouldable material may be distributed, wherein: an entranceway is formed in the mouldable material carrier, into which mouldable material may be urged, an internal cavity is formed within the mouldable material carrier, the internal cavity being connected to the entranceway; and a plurality of openings are formed in the first surface and are connected to the internal cavity such that, when mouldable material is urged into the entranceway, the mouldable material is received into the internal cavity and urged out of the openings to distribute mouldable material across the first surface.

The openings and internal cavity help to distribute the mouldable material evenly. A syringe may be provided with the mouldable material carrier (e.g. in a kit of parts) for injecting mouldable material into the mouldable material carrier. The syringe may contain a predefined amount of mouldable material to ensure that the appropriate amount of material is injected into the mouldable material carrier.

The entranceway may be centrally located in an opposite surface of the mouldable material carrier to the first surface. Alternatively, the entranceway may be located on a side wall of the mouldable material carrier. This can make it easier to syringe the mouldable material into the mouldable material carrier. The openings may be substantially evenly distributed across the first surface to provide an even distribution of mouldable material. Alternatively, the mouldable material carrier may be configured to distribute a larger amount of the mouldable material to the centre of the first surface (e.g. through the distribution of openings in the first surface, or the arrangement of the internal cavity).

The mouldable material carrier may be made of two or more parts (e.g. made out of injection moulded plastic) and combined together (e.g. via snap fittings, screws or other fastening means), or may be manufactured as a single part (e.g. via additive manufacturing).

Advantageously, the mouldable material carrier may further comprise: a connecting part for connecting the mouldable element carrier to a surgical guide production apparatus in a predetermined position and orientation; and/or fiducial markers to allow the position and/or orientation of the mouldable material carrier on the surgical guide production apparatus to be determined. This allows the various elements to be registered relative to each other. The connection to the surgical guide production apparatus can be via the surgical guide carrier mounted on the surgical guide production apparatus.

The mouldable material carrier may further comprise one or more protrusions or one or more indentations formed on an outer surface to provide a grip. The grip could be on a side or back wall of the mouldable material carrier to form a grip for holding the mouldable material carrier. Alternatively, or in addition, the grip may be on the first surface grip to help secure the mouldable material to the front surface. Mouldable material may harden around the protrusions (or in the indentations) to help secure the mouldable material to the mouldable material carrier.

Advantageously, the entranceway may be formed with a frusto-conical opening for the receipt of a syringe for supplying the mouldable material. This may be in the form of a countersink. This helps the user to align the syringe correctly within the entranceway and helps to provide a seal around the syringe when the syringe is fully inserted to avoid mouldable material escaping back out of the entranceway.

The internal cavity may be formed of a number of tunnels connecting the entranceway to the openings in the first surface.

Advantageously, the openings in the first surface may comprise one or more sets of openings, each set of openings comprising openings distributed in a star pattern around a corresponding central axis, and wherein internal tunnels connect each of the centrally located openings at a point along the central axis. This helps to distribute mouldable material evenly across the first surface. The star pattern may be some form of asterisk.

Advantageously, the internal cavity may be formed of one or more splitting sections, wherein each splitting section comprises an entry connected to the entranceway and opening into a splitting cavity through which the mouldable material may be urged, a barrier located over the entry to at least partially impede the progress of the mouldable material, and two or more exit openings located peripherally to the barrier such that, when mouldable material is urged through the entry, into the splitting cavity, the mouldable material is split and extruded through the corresponding exit openings. This helps to divide the mouldable material.

Advantageously, the barrier may fully cover the cross section of the entry (although the barrier is spaced away from the entry). By locating the barrier over the entry, the mouldable material is forced to fill the splitting cavity before being extruded out of the exit openings. This helps provide an even distribution of mouldable material. Multiple stages of splitting sections may be provided, with each exit opening for an earlier stage being connected to the entry for a corresponding later splitting section.

The exit openings may be located at equal distances from the centre of the barrier and may have equal area cross-sections so that the mouldable material is split into substantially equal volumes of mouldable material. This helps to provide an even distribution of mouldable material. Alternatively, the one or more splitting sections may be arranged to provide a greater volume of mouldable material to the centre of the first surface than to the periphery of the first surface.

According to a further aspect of the invention there is provided a surgical guide production apparatus for modifying an impression of a surgical site to produce a surgical guide, the surgical guide production apparatus comprising: a mount for releasably receiving an impression of a surgical site; a coupling portion configured to couple a cutting element to the surgical guide production apparatus; and a driving mechanism configured to drive the cutting element, when coupled to the coupling element, to modify the impression of the surgical site to produce a surgical guide, wherein, in use, the driving mechanism is located below the mount, such that debris from the impression falls away from the impression as it is being modified. Positioning the driving mechanism below the mount helps to remove debris from the impression/surgical guide.

The driving mechanism may comprise a motor for driving the cutting element (e.g. rotating the drill) and a motor for moving the cutting element into position and urging the cutting element into the mouldable material. The surgical guide production apparatus may further comprise a rotation mechanism upon which the mount is located, to rotate the mount around a tilt axis (running horizontally), and to rotate the impression around a yaw axis (running radially from the tilt axis). This allows the surgical guide production apparatus to position the impression appropriately for modification. The rotation mechanism may include a yaw axis drive member for rotating a rotatable section of the surgical guide carrier to rotate the impression mounted upon the surgical guide carrier about the yaw axis.

Advantageously, the surgical guide production apparatus may further comprise a protective barrier coupling mechanism configured to releasably couple a protective barrier to the surgical guide production apparatus, the protective barrier coupling mechanism comprising: a moveable portion configured to couple to a section of the protective barrier; and a positioning mechanism configured to move the portion from a first position that allows access to the mount and coupling portion to a second position in which the protective barrier is positioned around a cutting area containing the cutting element and the impression to help prevent contaminants from entering or leaving the cutting area during modification of the impression.

By positioning the driving mechanism below the mount and allowing a protective barrier to be positioned around the cutting area, debris from the modification can be effectively contained within the protective barrier and can be easily disposed of after modification.

Advantageously, the surgical guide production apparatus further comprises a securing section configured to releasably secure a second protective barrier to the surgical guide production apparatus in an arrangement around the mount to isolate the surgical guide from the mount. This helps to prevent debris from the surgical guide from contaminating the surgical guide production apparatus and prevents accidental contamination of user through accidental contact with the mount when loading/unloading the surgical guide.

The surgical guide production apparatus may further comprise: a sensor configured to read a coding element that attached to the cutting element and/or a surgical guide carrier for the impression, the coding element storing a code indicating one or more properties of the cutting element and/or one or more properties of the surgical guide carrier for the impression; a processor configured to: determine one or more properties from the code, compare the one or more properties to one or more expected properties; and in response to determining that the one or more properties match the one or more expected properties, allow the driving mechanism to be used to modify the mould; or in response to determining that the one or more properties do not match the one or more expected properties, prevent the driving mechanism from being used to modify the impression. This helps to prevent errors in production through the use of an incorrect attachment.

Further embodiments may be configured for use with a production apparatus for producing a bone graft or implant. This may be in addition to, or instead of, being configured for use with a surgical guide production apparatus. Equally, the production apparatus itself may be configured for one or both uses. For instance, the features described above with reference to the surgical guide production apparatus are equally applicable to a production apparatus for modifying a section of bone to produce a bone graft.

For instance, in accordance with an embodiment there is provided a cutting attachment for use on a surgical production apparatus, the cutting attachment comprising: a cutting element; a connector for connecting the cutting element to a drive mechanism of the production apparatus so that the cutting element can be driven by the drive mechanism to produce a surgical guide, surgical implant or surgical bone graft; and a protective barrier configured to be positioned around the cutting element to surround a cutting area to help prevent contaminants from entering or leaving the cutting area during modification of the impression.

Furthermore, in accordance with a further embodiment there is provided carrier for attaching to a surgical production apparatus, the carrier comprising: a connector for mounting the carrier to a mount on the production apparatus; a coupling portion for receiving and retaining: an impression of a surgical site so that, when the impression is retained in the carrier, and when the carrier is mounted on the production apparatus, the production apparatus can modify the impression to produce a surgical guide or surgical implant; or a section of bone so that, when the section of bone is retained in the carrier, and when the carrier is mounted on the production apparatus, the production apparatus can modify the section of bone to produce a bone graft; and a protective barrier configured to be positioned around at least part of the production apparatus to provide a barrier between the mount and at least part of the production apparatus.

According to a further aspect of the invention there is provided a production apparatus for modifying a section of bone to produce a bone graft. The production apparatus comprises a mount for receiving the section of bone; a surface configuration recorder for recording a configuration of a surface of an section of bone received by mount to produce surface data for registering that section of bone with the production apparatus and with a planned bone graft shape; a cutting element or a coupling portion configured to couple a cutting element to the production apparatus; and a driving mechanism configured to drive the cutting element, when coupled to the coupling element, to shape the section of bone to match at least part of the planned bone graft shape.

This allows a bone graft to be more accurately shaped based on a planned bone graft shape. The section of bone may be an excised or resected portion of bone taken from the patient for use in producing the bone graft. The planned bone graft shape may be determined based on image data of anatomical features of the patient (e.g. CT or MRI image data) and/or a scan of a mould of the surgical site. This ensures a better fit for the bone graft to reduce movement within the surgical site when fitted.

The surface configuration recorder may be a scanner (e.g. an optical scanner) for determining the geometrical shape of the surface of the section of bone. The surface of the bone may be represented either via a surface model or volumetric model. The surface data may be utilised to determine an overall geometric model of the section of bone. The cutting element may be configured to cut, mill or drill. The mount may be configured to reliably receive the section of bone. This may be via one or more clips, clamps, screws, or other mounting means.

The production apparatus may cut away bone to shape the bone in accordance with at least part of the planned bone graft. For instance, substantially one side of the bone may be shaped before the bone is flipped (e.g. mounted on its reverse side) to allow the opposite side to be shaped.

According to an embodiment the production apparatus further comprises a mount for holding a set of cutting elements, wherein the production apparatus is configured to change between cutting elements. This allows different tools to be used when modifying the bone section. For instance, a rack of tools may be located within the production apparatus and the coupling portion may be mounted on a movable arm. The movable arm may be configured to move the coupling portion to deposit a cutting element mounted on the coupling portion on the rack/mount and retrieve a new cutting element from the rack/mount. The various cutting elements may include, for instance, cutting elements for cutting, sawing, milling or drilling. This avoids the need for user intervention during the modification of the bone and therefore reduces the risk of injury by the user (from the cutting elements) and reduces the risk of contamination of the bone graft, production apparatus or user.

According to an embodiment the production apparatus further comprises a processor configured to determine the planned bone graft shape based on image data representing anatomical features of the anatomy of the patient.

According to a further embodiment the mount is configured to receive a mould of a surgical site and the surface configuration recorder is configured to record the configuration of a surface of the mould to produce mould surface data for determining the planned bone graft shape based on the mould surface data and image data representing anatomical features of the anatomy of the patient.

According to a further embodiment the production apparatus further comprises a processor configured to determine the planned bone graft shape based on the mould surface data and the image data representing anatomical features of the anatomy of the patient.

By registering the shape of a mould of the surgical site the bone graft may be shaped to more accurately fit the surgical site. For instance, soft tissue may not have been fully removed from the surgical site, and may cause issues fitting a bone graft prepared based solely on image data of the anatomical features of the patient (e.g. showing bone and hard tissue). Furthermore, by taking a mould of the surgical site, the bone graft can be shaped to fit features that have been added to the surgical site during surgery. For instance, a section may be cut from the bone within the surgical site into which the bone graft may be fitted. Alternatively, one or more prostheses may have already been fitted within the surgical site. By taking a mould of the surgical site, the bone graft can be shaped to more accurately fit these features of the surgical site and therefore improve registration with the surgical site reduce movement within the surgical site.

The mould may be releasably received in the same manner that the section of bone may be releasably received.

The production apparatus may be further configured to modify a mould of the surgical site to produce a surgical guide.

According to a further aspect of the invention there is provided a kit of parts for producing a surgical guide comprising any combination of: a production apparatus as described above; a cutting attachment as described above; a surgical guide carrier as described above; and a mouldable material carrier as described above.

DETAILED DESCRIPTION

Embodiments of the invention aim to solve the problem of how to maintain sterility of a surgical guide, and the surrounding operating theatre, during intraoperative production.

FIG. 1 shows a production apparatus in accordance with an embodiment of the invention. The production apparatus 100 is configured to modify an impression of a surgical site to produce a surgical guide. The production apparatus 100 is intended to be used within the operating room and situated next to the operating table. The embodiments described herein ensure that sterile personnel such as the scrub nurse and surgeon are able to use the production apparatus and surgical guides without compromising sterility.

The production apparatus 100 comprises a coupling portion 112 configured to couple to a replaceable cutting attachment 200 and a mounting point 110, upon which a surgical guide carrier 300 may be mounted. The surgical guide carrier 300 is a removable mounting point for a surgical guide. The surgical guide carrier 300 is configured to secure an impression of a surgical site to the production apparatus 100 in a predefined position and orientation. The production apparatus 100 includes a scanner 150 for scanning a surface of the impression.

The production apparatus 100 is configured to scan the surface of the impression and compare this to a stored medical scan of the patient's anatomy. This medical scan may be an MRI scan, a CT scan, or any other scan capable of recording the patient's anatomy. The scan of the surface of the impression may be an optical scan or any other scan capable of measuring the geometry of the surface of the impression.

The production apparatus 100 is configured to register the impression to the anatomical features of the patient. This allows the production apparatus 100 to determine where surgical guide holes need to be drilled into the impression in order to produce a surgical guide according to a predetermined surgical plan.

The registration process allows the production apparatus 100 to calibrate itself with respect to the impression in order to ensure that guide holes are drilled in the correct position.

The general process of scanning and modifying an impression of the surgical site using a production apparatus is discussed in more detail in WO 2015/075423 A1 (the entirety of which is hereby incorporated by reference).

The overall system according to the embodiments described herein comprises the production apparatus 100 and a number of single-use, sterile packed accessories to ensure that the sterile environment in the operating theatre is maintained.

A first accessory consists of a cutting attachment 200 (in the present case, a drill attachment) with an integrated sterile barrier drape (shown in FIGS. 4-8). For clarity, the barrier drape is not shown in FIG. 1. The cutting attachment 200 can be releasably mounted on to the production apparatus 100 at the coupling portion 112 of the production apparatus 100. The coupling portion 112 is connected to a motor for driving the cutting attachment 200.

The coupling portion 112 is located on a movable arm. The production apparatus is configured to be able to move the movable arm along three orthogonal directions, x, y and z (shown in FIGS. 1 and 2). This allows the production apparatus 100 to position the cutting attachment 200 in to the correct position and to drive the cutting attachment 210 into the impression to produce a surgical guide hole within the impression at the required location.

Figure 9:
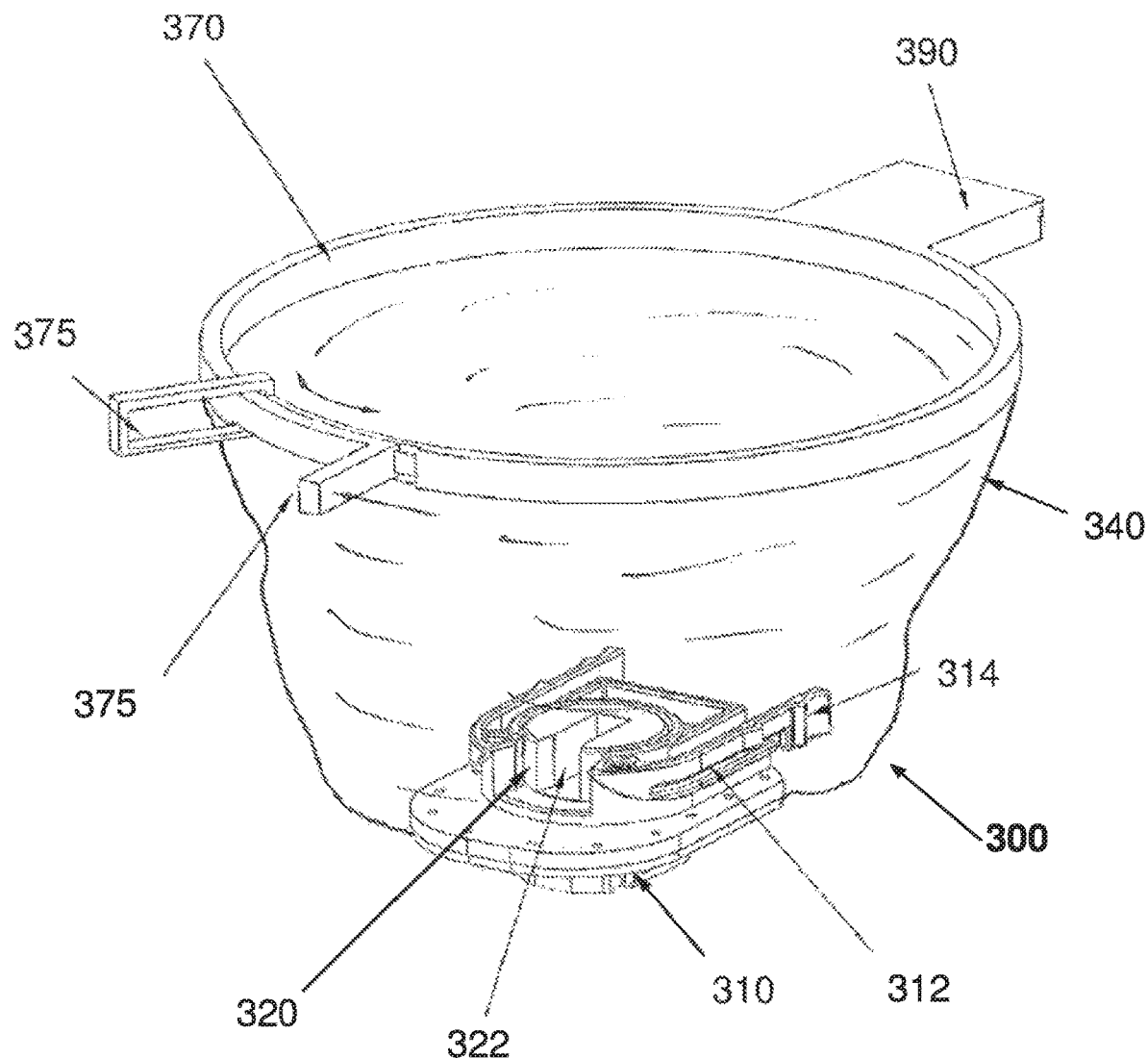
FIG. 9 shows a surgical guide carrier with integrated barrier drape according to an embodiment.
Figure 10A:
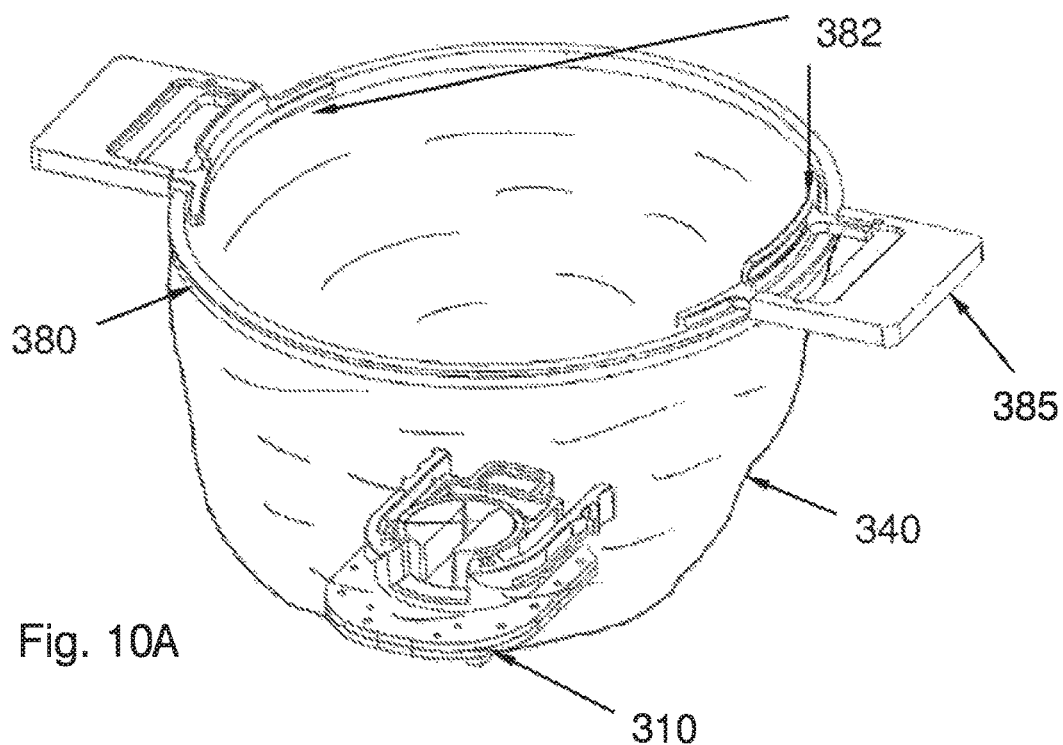
FIGS. 10A and 10B show a surgical guide carrier with integrated barrier drape according to an alternative embodiment.
Figure 10B:
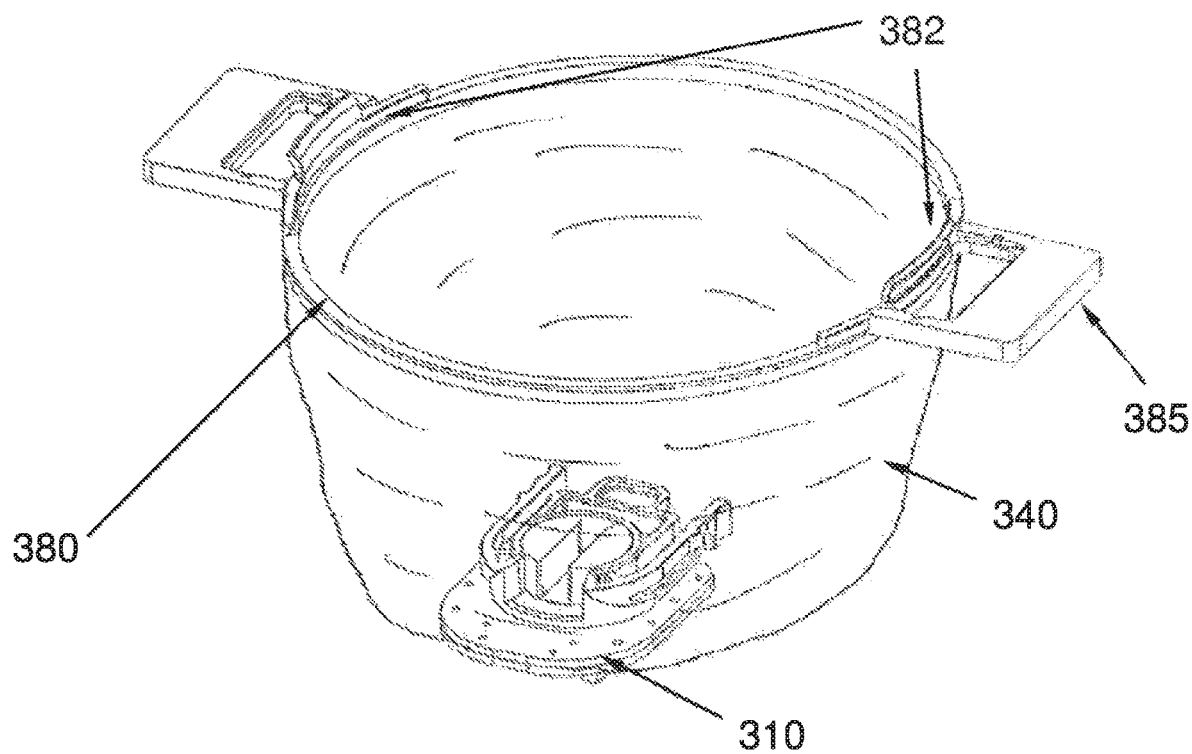
Figure 11:
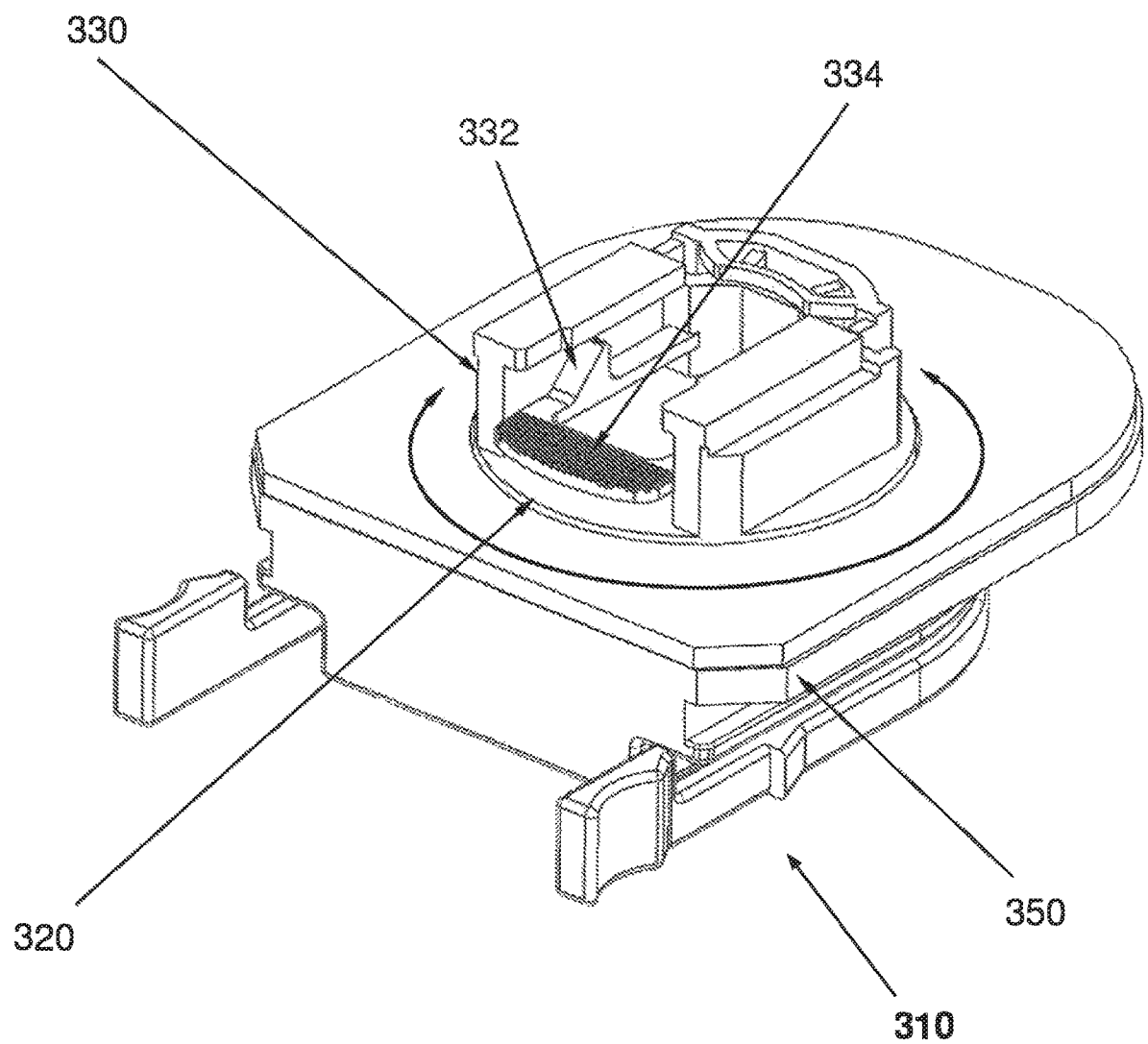
FIG. 11 shows a detailed view of a front side of a carrier part of the surgical guide carrier.

A second accessory consists of a surgical guide carrier 300 with an integrated sterile barrier drape (shown in FIGS. 9-11). For clarity, the barrier drape is not shown in FIGS. 1-3. The surgical guide carrier 300 can be releasably mounted upon a mounting point 110 on the production apparatus 100. The mounting point 110 is attached to a gimbal 140 of the production apparatus 100. The gimbal 140 forms part of a rotation mechanism that includes a motor that is configured to rotate the mounting point, and the surgical guide carrier 300, about a tilt axis running parallel to the ground (along the horizontal plane).

The rotation mechanism further comprises a yaw axis drive member, located on the gimbal, that is configured to mate with a yaw axis keyway in the surgical guide carrier 300 to rotate a rotatable section of the surgical guide carrier about a yaw axis running radially from the tilt axis.

The rotation mechanism therefore allows the production apparatus 100 to rotate a surgical guide carrier 300 itself about the tilt axis, and rotate the impression of the surgical site about the yaw axis, to move the impression into the correct orientation to allow a surgical guide hole to be formed along the correct line.

The gimbal 140 also allows the production apparatus 100 to rotate the surgical guide carrier 300 into a forward orientation to allow the surgical guide to be coupled and uncoupled from the production apparatus 100 and to rotate the surgical guide carrier 300 to a backward orientation to allow the production apparatus 100 to scan the surface of an impression of the surgical site to produce a plan for modifying the impression.

The mounting point 110 is located above the coupling portion 112 so that, when the impression is being modified, debris from the impression falls downwards, away from the impression and towards the cutting element.

A third accessory consists of a mouldable material carrier (shown in FIGS. 12-15). The mouldable material carrier allows an impression of a surgical site to be taken and forms part of the surgical guide when the impression has been modified. The mouldable material carrier comprises a number of channels so that mouldable material may be injected into the mouldable material carrier and evenly distributed across a front surface of the mouldable material carrier.

Figure 14:
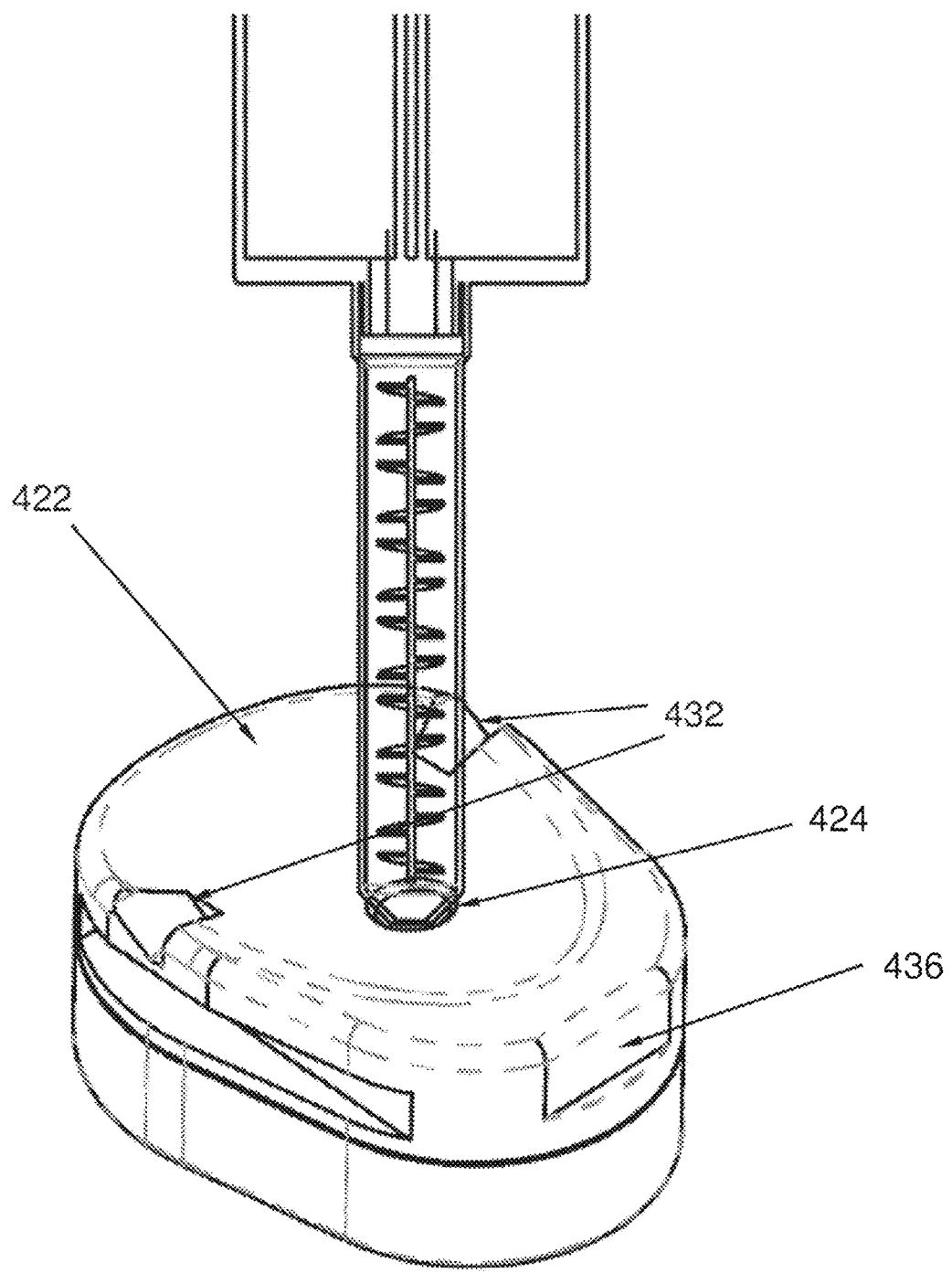
FIG. 14 shows a perspective view of a syringe injecting mouldable material into the mouldable material carrier.
Figure 15:
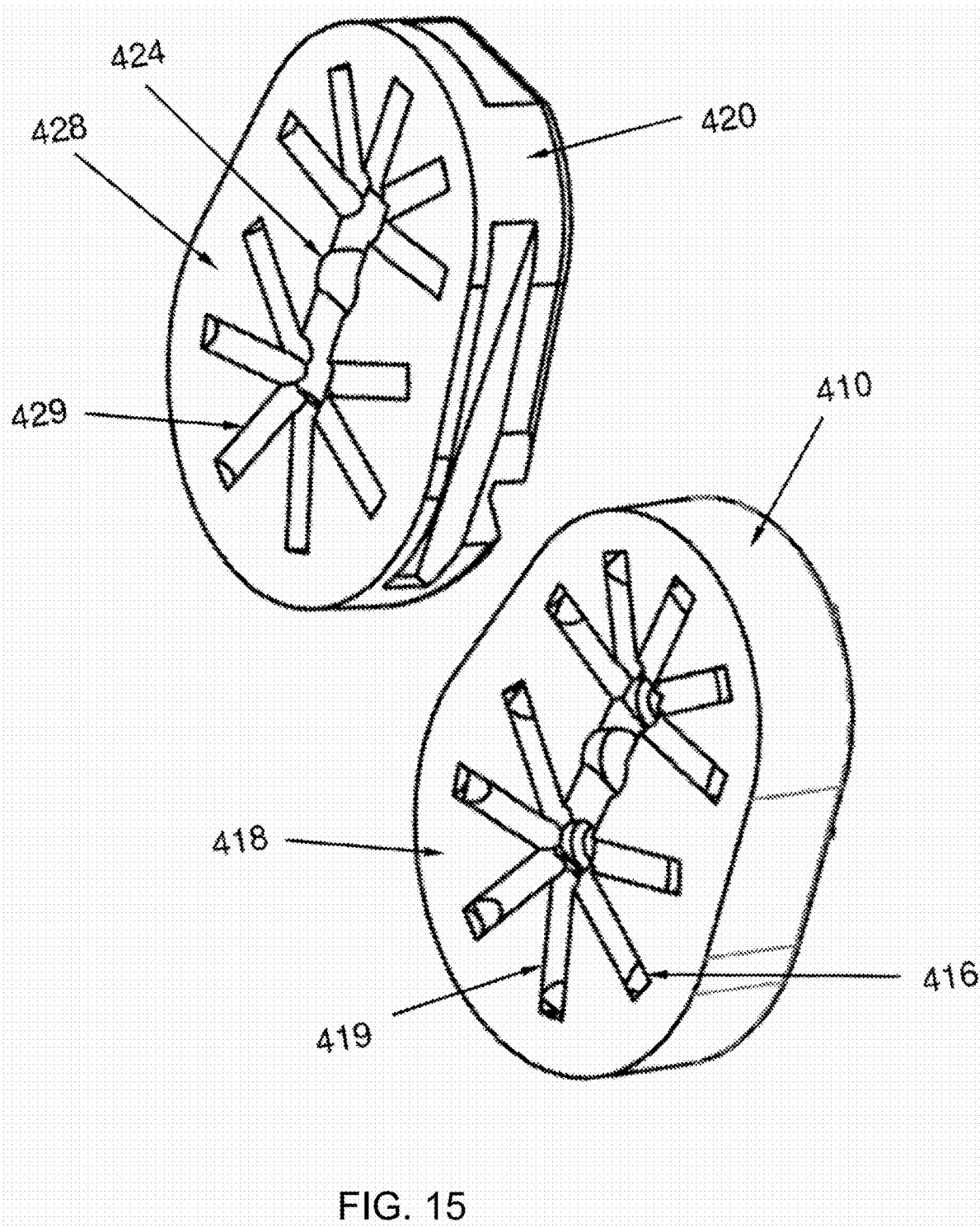
FIG. 15 shows the internal structure of the mouldable material carrier.

A further accessory comprises a mouldable material dispenser and mouldable material (shown in FIGS. 14 and 15). This can be used to dispense mouldable material onto the surgical guide.

An impression of a surgical site can be taken using mouldable material dispensed onto the mouldable material carrier. The mouldable material carrier and impression can then be coupled to the production apparatus 100 via the surgical guide carrier when the surgical guide carrier is mounted on the production apparatus 100. The production apparatus 100 can then scan the impression of the surgical site and modify the impression with the cutting attachment 200.

Preparation of the production apparatus 100 can be carried out by a sterile scrub nurse. The individual accessories can be supplied either double pouched or in a blister pack arrangement. The circulating nurse can then open the outer packaging allowing the sterile accessories to be transferred aseptically for use by the scrub nurse.

The purpose of the sterile packed accessories is to simplify the process of using the production apparatus within the surgical environment. The accessories ensure that a protective sterile barrier is maintained between the non-sterile parts of the production apparatus and the users. In addition, the accessories ensure that debris generated from modification of the surgical guide is isolated within the boundaries of the single use accessories. This means that, after surgery, the accessories can be quickly and easily removed from the production apparatus, without the risk of biological material being transferred to the production apparatus or other parts of the operating room. This improves preparation time and avoids lengthy, costly reprocessing and its associated risks.

Figure 2:
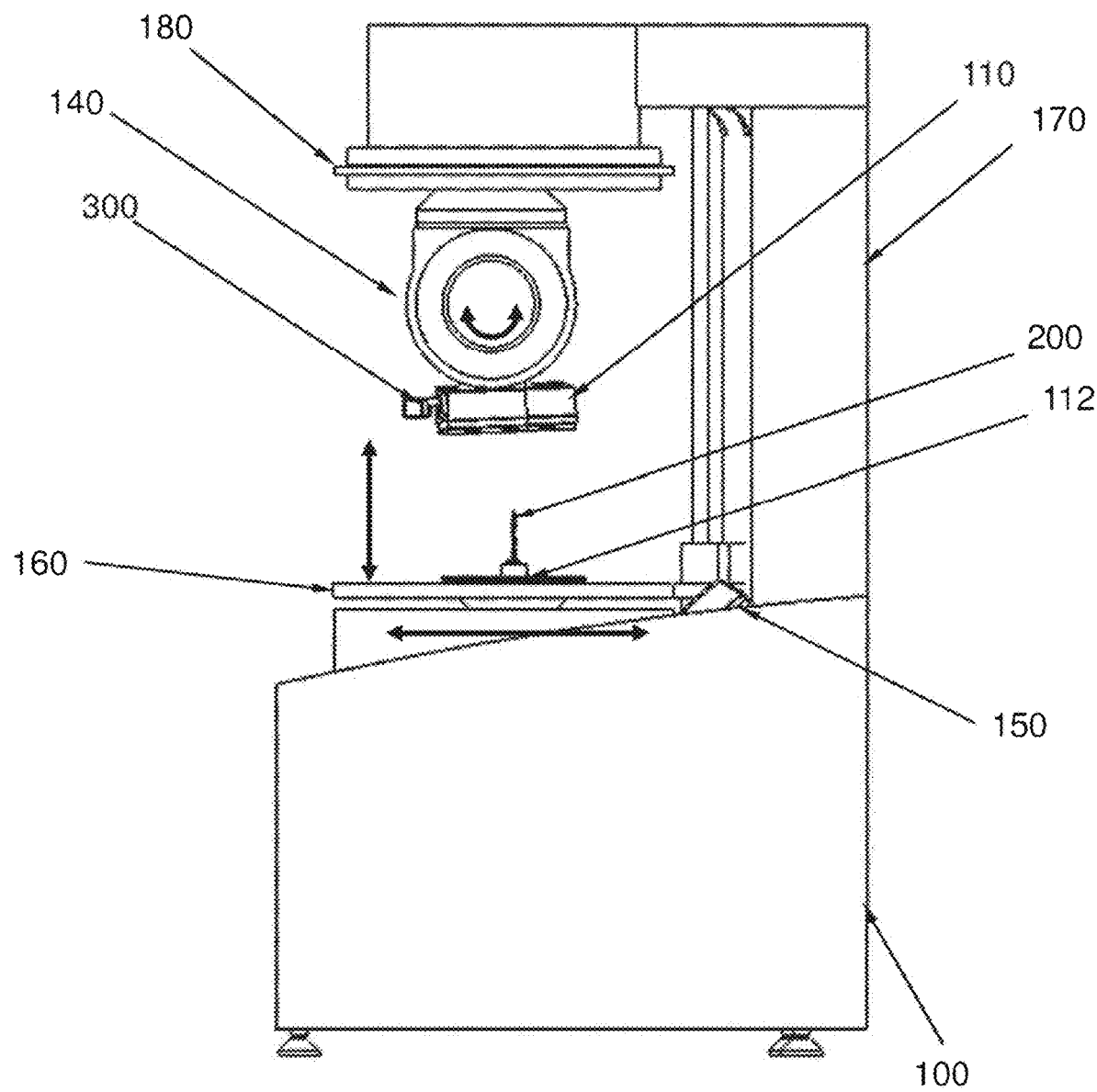
FIG. 2 shows a side view of the production apparatus.

FIG. 2 shows a side view of the production apparatus. Again, the barrier drapes for the cutting attachment 200 and surgical guide carrier 300 are not shown. The gimbal 140 is located directly above the coupling portion 112 for the cutting attachment 200. This defines a cutting area, between the coupling portion 112 and the gimbal 140. When the barrier drapes are in position, a sterile zone is located in the region of this cutting area.

As the gimbal 140 (upon which the mounting point is attached) is located directly above the coupling portion 112, debris from the drilling falls downwards, away from the mounting point when the impression is being modified by the cutting attachment 200. This helps remove debris from the surgical guide, as the surgical guide is being formed/modified. This also helps keep the debris within the confines of the barrier drapes, and helps collect the debris in the barrier drape for the cutting attachment so that it may be easily collected and disposed of after the surgical guide has been completed. This ensures that there is no cross-contamination from one procedure to the next.

As discussed, the cutting attachment 200 includes a barrier drape. This is in the form of an elongated tube attached at one end to a central housing of the cutting attachment 200. An outer edge of the elongated tube can be secured around a driven support ring 160 of the production apparatus 100. The driven support ring 160 is connected to an upwardly extending arm 170 of the production apparatus 100.

The production apparatus 100 is configured to raise the driven support ring 160 from a lower, retracted position (as shown in FIGS. 1 and 2), wherein the driven support ring 160 is proximal to the coupling portion, to an upper, extended position, in order to lift the barrier drape for the cutting attachment 200 to seal off the cutting area. This prevents debris from the drilling from escaping the cutting area and contaminating the operating theatre. In the upper position, the driven support ring 160 is proximal to the gimbal 140.

The production apparatus 100 further comprises an upper housing lip 180. The upper housing lip 180 provides an outwardly projecting lip over which the barrier drape for the surgical guide carrier 300 may be secured. This isolates the rotation mechanism from the cutting area to prevent debris from the surgical guide from clogging the rotation mechanism and to prevent contaminants from the rotation mechanism from falling into the cutting area and contaminating the surgical guide. In addition, this provides a sterile barrier to avoid accidental contamination of the user through contact with the rotation mechanism when the user is attaching or detaching a surgical guide.

Accordingly, when in place, the barrier drapes isolate moving parts of the production apparatus (which are difficult to sterilise) from the sterile cutting area, to avoid contamination of the surgical guide and/or the user.

Figure 3:
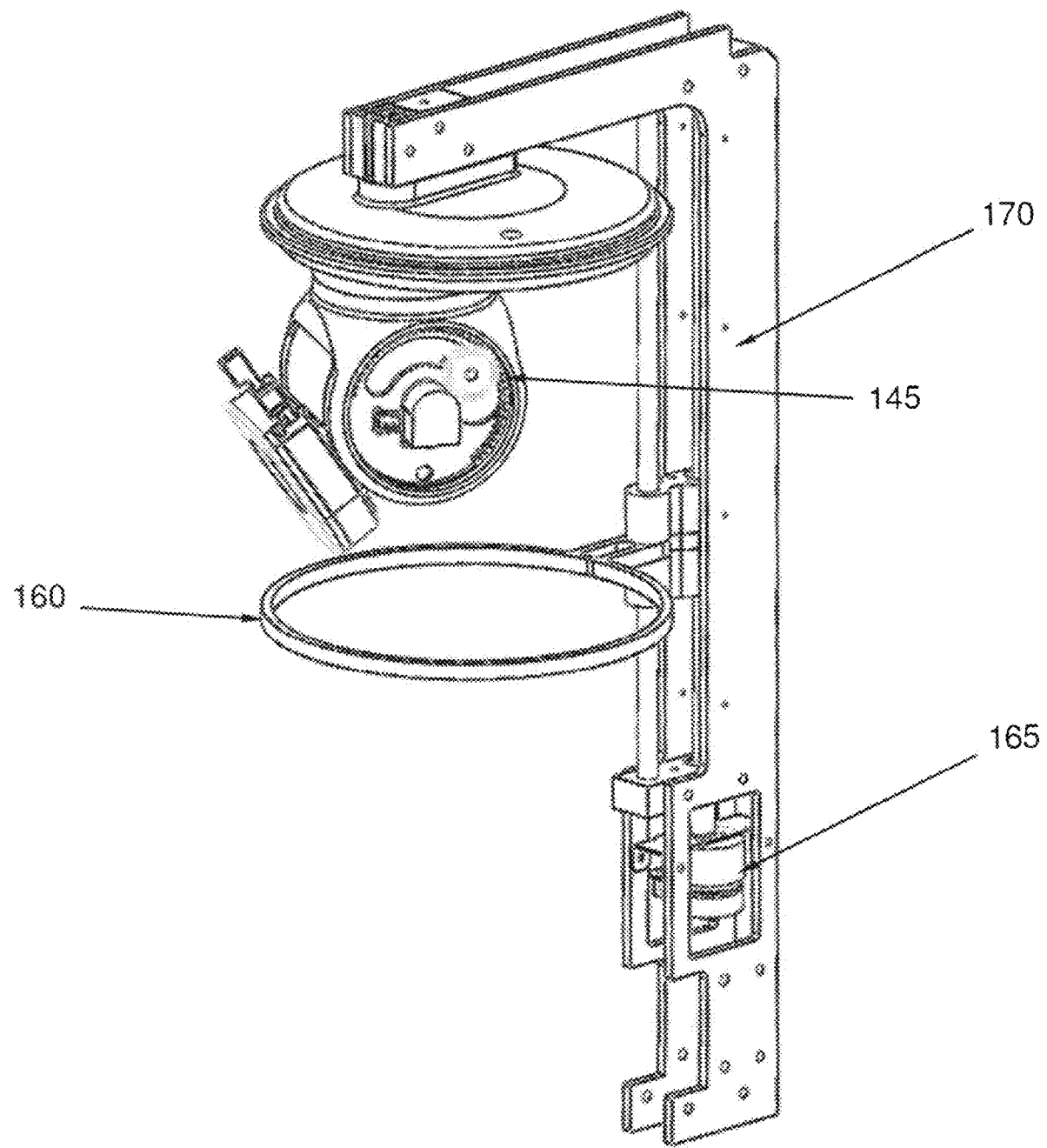
FIG. 3 shows an internal support mechanism of the production apparatus.

FIG. 3 shows an internal support mechanism of the production apparatus. The driven support ring 160 is shown raised mid-way up the upwardly extending arm 170. A motor 165 is located within the housing of the production apparatus 100 for raising and lowering the driven support ring 160. Similarly, a motor 145 is located within the upper housing of the production apparatus 100, supported by the upwardly extending arm 170, for driving the gimbal 140.

Figure 4:
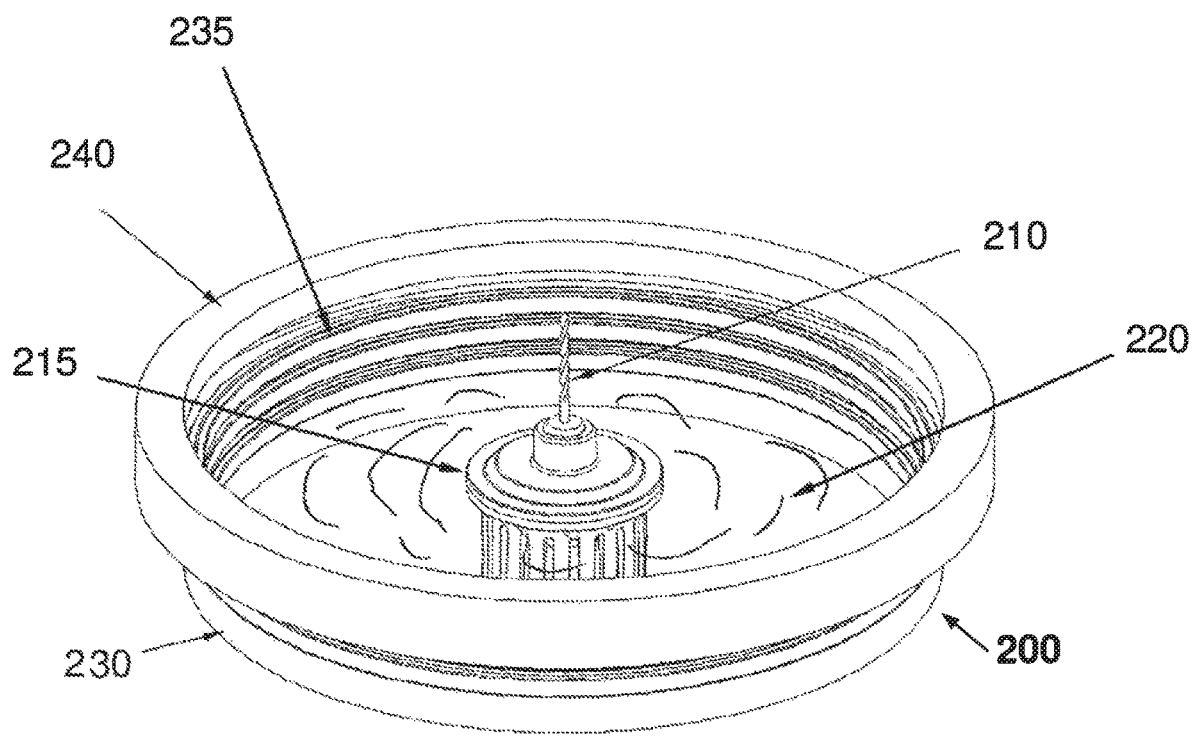
FIG. 4 shows a cutting attachment with integrated barrier drape according to an embodiment.

FIG. 4 shows a cutting attachment with integrated barrier drape according to an embodiment. The cutting attachment 200 comprises a centrally located cutting element 210. In this case, the cutting element is a drill bit. Cutting elements of various types, (e.g. drill bits, saw blades, and different sized cutting elements) may be utilised. Accordingly, a different cutting attachment (including integrated barrier drape) may be provided for different cutting elements for different uses. The various cutting elements may be made of stainless steel or any other appropriate durable material.

The cutting element 210 is mounted on a central housing 215, such that the cutting element 210 may be driven to rotate by the production apparatus 100. The central housing 215 is configured to couple to the coupling portion of the production apparatus 100.

The cutting attachment 200 further comprises a barrier drape 220 shown in FIG. 4 as a transparent sheet. The barrier drape 220 is secured centrally around the entirety of the outside of the central housing 215. The barrier drape 220 extends radially outwards from the central housing to a lower ring 230 that encircles the central housing 215. The barrier drape 220 is secured to the lower ring 230.

An upper ring 240 is located above the lower ring 230. An outer end of the barrier drape 220 is attached to the upper ring 240. The upper ring 240 comprises a coupling section for securing the upper ring 240 to the driven support ring 160 of the production apparatus 100. This allows the barrier drape 220 to be lifted up around the cutting area of the production apparatus 100 by the driven support ring 160. The lower ring 230 is configured to weigh down the base of the barrier drape 220 and to support the barrier drape 220 to keep the barrier drape 220 taught to avoid the barrier drape 220 from sagging, or being blown, into the cutting area. To this end, intermediate support rings 235 are connected to the barrier drape 220 between the upper 240 and lower 230 rings. The upper 240, lower 230, and intermediate 235 support rings are generally support frames and may be of any appropriate shape to prevent the barrier drape 220 from encroaching on the cutting area.

Whilst this embodiment relates to a drill attachment including a drill bit, alternative attachments with alternative cutting elements may be implemented with similar barrier drapes in accordance with embodiments of the invention. Alternative cutting elements may include saws for cutting slots, burs or reamers for cutting larger holes, or any other cutting element.

Figure 5:
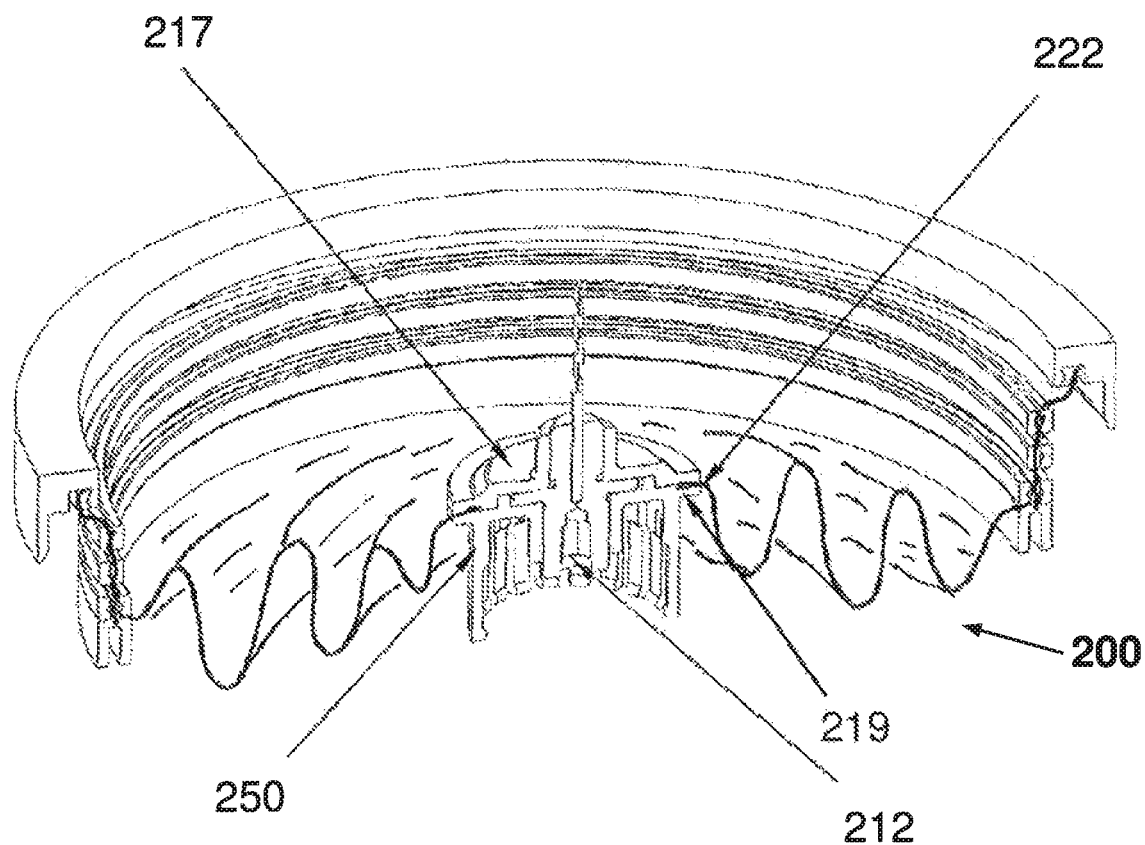
FIG. 5 shows a cross-section of the cutting attachment with the barrier drape in a retracted arrangement.

FIG. 5 shows a cross-section of the cutting attachment with the barrier drape in a retracted arrangement. The central housing 215 comprises front 217 and rear 219 housings. The front 217 and rear 219 housings may be formed from injection-moulded plastic. The barrier drape 220 is secured at an inner edge 222 between the front 217 and rear 219 housings.

A coupling section 212 is connected to the cutting element 210 and configured to mate with a corresponding coupling section of the production apparatus 100 so that the production apparatus 100 may drive the cutting element 210.

The barrier drape 220 passes through the upper 240, lower 230, and intermediate 235 support rings so that the support rings 230, 235, 240 hold the barrier drape 220 away from the cutting area.

A coding element 250 is located within the rear housing 219. The coding element 250 includes an indication of the type of cutting element 210 incorporated into the cutting attachment 200. The coding element 250 is readable by a sensor in the production apparatus 100 so that the production apparatus can confirm that the correct cutting element 210 is attached.

The production apparatus 100 is configured to disable the driving mechanism for the cutting element in response to a determination that an incorrect cutting element 210 is attached. Equally, the production apparatus 100 is configured to enable the driving mechanism for the cutting element in response to a determination that the correct cutting element 210 is attached.

The coding element 250 may be a radio-frequency identification (RFID) chip, a barcode, QR code, memory device (e.g. flash), or any other form of machine-readable media. For instance, the coding element may encode the type of cutting element via its physical shape, which may be read by the production apparatus via, for instance, an optical sensor, or a configuration of buttons.

Coding elements can indicate different types of cutting attachment, including different types of cutting element (e.g. drill, bur, etc.), different lengths or diameters of cutting element, different materials of the cutting element and/or different manufacturers of the cutting attachment.

Figure 6:
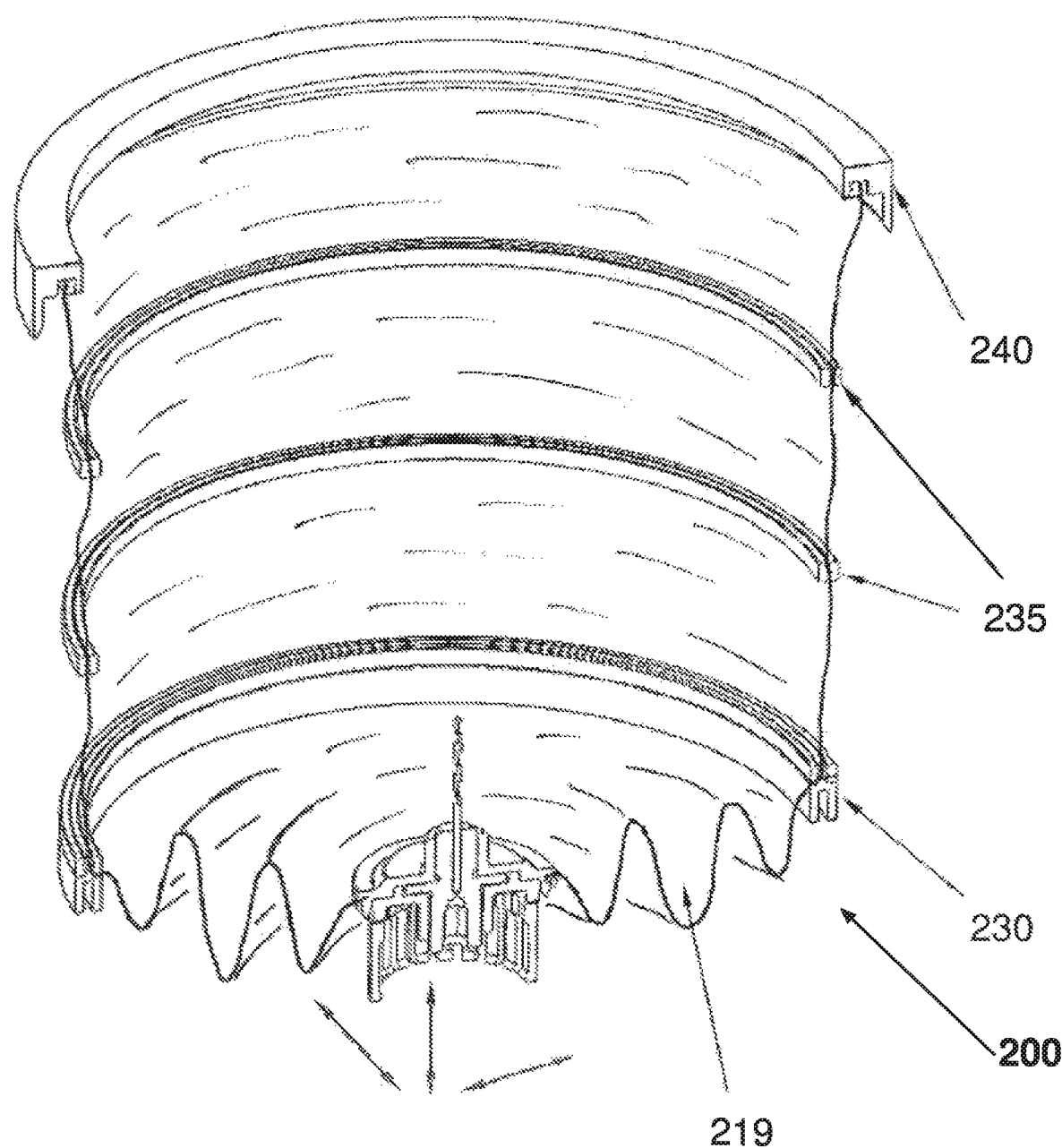
FIG. 6 shows a cross-section of the cutting attachment with the barrier drape in an extended arrangement.

FIG. 6 shows a cross-section of the cutting attachment with the barrier drape in an extended arrangement. The upper ring 240 has a lip so that it may be secured over the driven support ring 160 of the production apparatus 100.

As the driven support ring 160 raises the upper ring 240, the barrier drape 220 is raised, along with the intermediate support rings 235. At full extension of the barrier drape 220, the intermediate support rings 235 are spaced in between the upper 240 and lower 230 support rings.

The barrier drape 220 has a degree of slack between the lower support ring 230 and the central housing 215. This allows the central housing 215 and cutting element 210 to be moved by the production apparatus 100 along three orthogonal axes, x, y and z.

The lower support ring 230 is configured to weigh down the barrier drape 220 to ensure that the section of the barrier drape 220 between the lower support ring 230 and the central housing 215 is not lifted as the upper support ring is lifted. This helps to keep the barrier drape 220 taut between the lower 230 and upper 240 support rings to prevent the barrier drape 220 from impinging on the cutting area. This also helps to maintain the slack around the cutting attachment to allow it to be moved. Alternatively, or in addition, lower support ring 230 may comprise a coupling section for securing the lower support ring 230 to the production apparatus 100 to prevent the lower support ring 230 from being raised as the upper support ring 240 is raised.

The x and y axes are located along the horizontal plane. Movement along these axes allows the production apparatus 100 to position the cutting element 210 along the correct line to modify the impression of the surgical site to produce the required surgical guide hole.

The z-axis is directed perpendicular to the horizontal plane. Movement along the z-axis allows the production apparatus 100 to urge the cutting element 210 into the impression to modify the impression. The sterile drape 210 is therefore baggy enough between the lower supporting ring 230 and the central housing 215 to allow the cutting element 210 to be raised all the way up into the impression of the surgical site.

Figure 7:
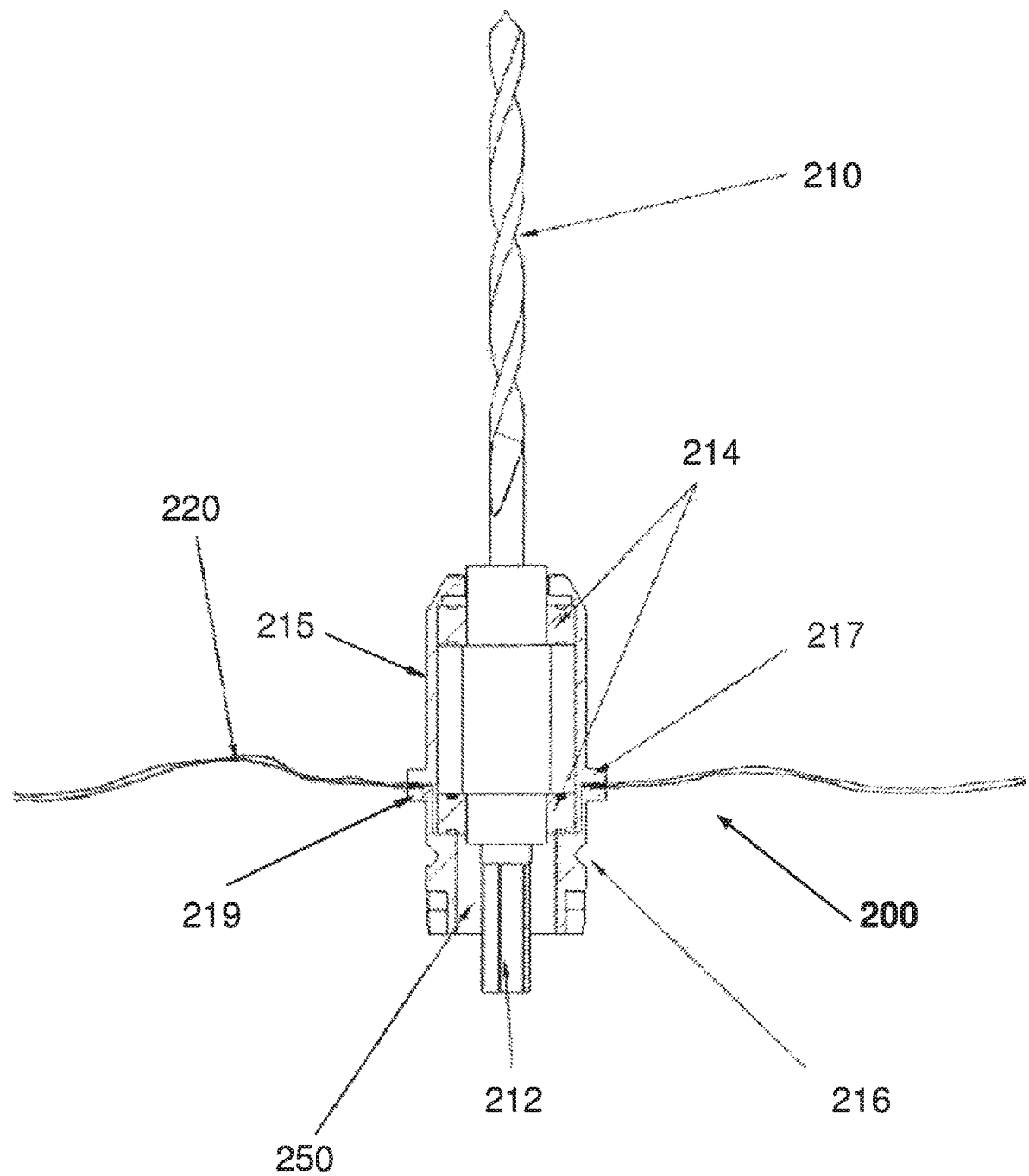
FIG. 7 shows a detailed cross-section of the drill and connecting portions of the cutting attachment.

FIG. 7 shows a detailed cross-section of the drill and connecting portions of the cutting attachment. The cutting element 210, in this case a drill bit, has a cutting section at a distal end and a coupling section 212 at a proximal end.

The coupling section 212 of the cutting element 210 is arranged to mate with a corresponding coupling section of the production apparatus 100. The coupling section 210 has drive faces that are configured to receive driving forces from the production apparatus to drive the cutting element 210.

Ball bearings 214 are located within the central housing 215. The ball bearings hold the cutting element 210 within the central housing 215, whilst allowing the cutting element 210 to be driven to rotate within central housing 215.

The rear housing 219 comprises a locking feature 216 located on an external surface of the rear housing 219. This allows the cutting element 210 to be locked into place in the coupling section of the production apparatus 100 via a corresponding locking mechanism in the production apparatus 100.

A coding element 250 is located within the rear housing 219 to enable the production apparatus 100 to identify various properties of the cutting element 210 to verify that the appropriate cutting element 210 is fitted.

Figure 8:
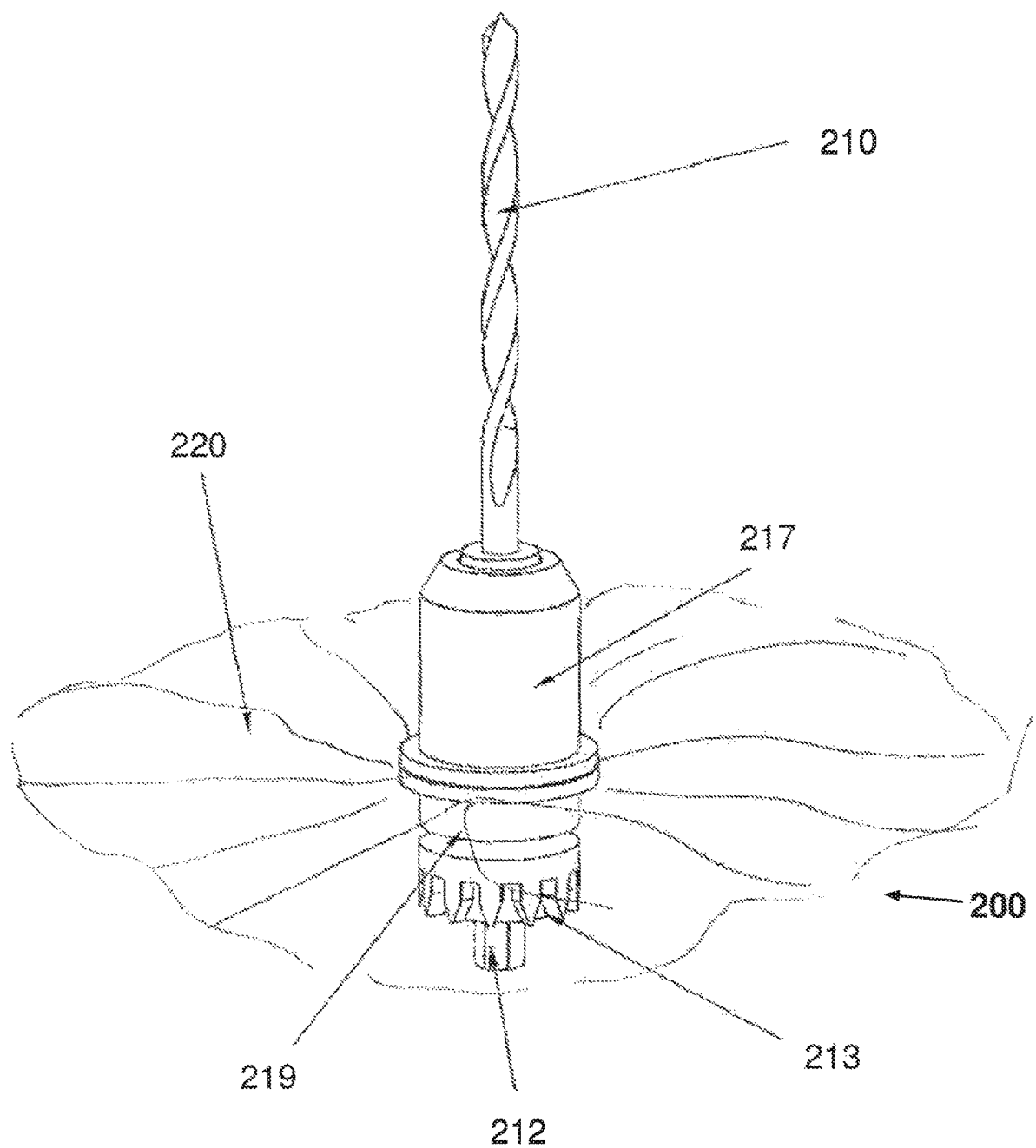
FIG. 8 shows a detailed perspective view of the drill and connecting portions of the cutting attachment.

FIG. 8 shows a detailed perspective view of the drill and connecting portions of the cutting attachment. The rear housing 219 includes static location features 213 at the proximal end of the cutting attachment 200. Static location features 213 comprise pointed protrusions with sloped faces that help urge the cutting attachment 200 into the correct position in the coupling section of the production apparatus 100. Accordingly, the static location features 213 are configured to be received within corresponding cavities of the coupling section of the production apparatus 100. The static location features 213 also provide purchase for the rear housing 219 to prevent the rear housing from rotating when the cutting element 210 is being driven.

FIG. 9 shows a surgical guide carrier with integrated barrier drape according to an embodiment. The surgical guide carrier 300 includes a carrier part 310, a barrier drape 340 connected to the carrier part 310 and an upper support ring 370 connected to the barrier drape 340.

The carrier part 310 comprises a connection portion for securing the carrier part 310 to the production apparatus 100. In the present embodiment, the connection portion comprises a pair of grooves 312 for receiving corresponding interlocking parts of the production apparatus 100. The grooves 312 allow the carrier part 310 to be slid into position on the production apparatus 100. This allows the carrier part 310 to be secured to the production apparatus 100 in a predetermined position and orientation so that the production apparatus 100 can register itself to the carrier part 310.

The connection portion further comprises a pair of release levers 314 that are configured to allow the carrier part 310 to be removed from the production apparatus 100 when the release levers 314 are urged towards each other. The release levers 314 include teeth that secure the carrier part 310 into position on the production apparatus 100 when the carrier part 310 is correctly located on the production apparatus 100 and when the release levers 314 are released.

The carrier part 310 comprises a rotatable portion 320. The rotatable portion 320 is a rotatable platform configured to be able to rotate within the carrier part 310 around a yaw axis. The carrier part 310 is configured to secure a surgical guide at a front section of the rotatable portion 320. The rotatable portion 320 comprises a yaw axis keyway 322 on a rear side (opposite to the front side) that is configured to mate with a yaw axis drive member of the production apparatus 100 so that the production apparatus 100 can drive the rotatable portion 320 to rotate about the yaw axis (the yaw axis running from perpendicular to the front and rear sides).

The barrier drape 340 is secured to the carrier part 310 between front and back housings of the carrier part 310. The barrier drape 340 surrounds the carrier part 310, forming a barrier that prevents debris from passing from the front side of the carrier part 310 of the rear side of the carrier part 310.

The barrier drape 340 is substantially in the shape of a hollow hemisphere, with a hole located at the centre into which the carrier part 310 is secured. An upper support ring 370 is connected to the rim of the hemisphere. This allows the barrier drape 340 to be lifted over the gimbal 140 of the production apparatus 100 and secured over the upper housing lip 180 of the production apparatus 100.

The upper support ring 370 is expandable to allow it to be passed over the upper housing lip 180 of the production apparatus 100; however, it is biased towards a smaller radius in order to secure the barrier drape over the upper housing lip 180. To achieve this, the upper support ring 370 comprises a partially overlapping spiral of resilient material. This may be formed of plastic. An inner end of the spiral is located radially inwards of an outer end of the spiral.

The inner and outer ends each comprise corresponding radially protruding levers 375. The lever 375 of the inner end comprises a passageway through which the outer end passes. When the two levers are urged towards each other, the diameter of the upper support ring 370 is increased, allowing the upper support ring 370 to be passed over the upper housing lip 180 of the production apparatus 100. The upper support ring 370 is resilient and therefore is biased to return to an arrangement with a diameter less than that of the upper housing lip 180 to secure the upper support ring 370 in place.

The upper support ring 370 also includes a radially protruding handle 390. This allows the user to lift the upper support ring 370 over the upper housing lip 180 of the production apparatus, whilst keeping their hands separated from non-sterilised portions of the production apparatus 100.

In an alternative embodiment the levers 375 have a sufficient length to be grasped by a user and are configured to support the weight of the surgical guide carrier 300 so that they may act as the handle for the upper support ring 370, so that a separate handle need not be provided.

Whilst the connection portion of the carrier part 310 of the above embodiment provides a means of securing the carrier part to the production apparatus 100 in a predetermined orientation, this is not essential. In an alternative embodiment, the connection portion may simply connect the carrier part 310 to the production apparatus such that the rotatable portion 320 may be rotated around the yaw axis. The connection portion may allow the carrier part to be connected in any, or at least, need not require a specific orientation. In this embodiment, fiducial markers are provided on carrier part to allow the production apparatus to determine the orientation of the carrier part 310, or at least the orientation of the rotatable portion 320, by scanning the fiducial markers.

FIGS. 10A and 10B show a surgical guide carrier with integrated barrier drape according to an alternative embodiment. The surgical guide carrier of this embodiment has a similar barrier drape 340 and carrier part 310 to those of the embodiment of FIG. 9. Having said this, the embodiment of FIGS. 10A and 10B has a different form of upper support ring 380.

In this embodiment, the upper support ring 380 comprises a frame with an opening of a fixed diameter that is larger than the diameter of the upper housing lip 180 to allow it to pass over the upper housing lip 180. To secure the upper support ring 380 over the upper housing lip 180, the upper support ring 380 further comprises a pair of opposing locking members 382 that radially protrude into the opening of the frame. The locking members 382 are located on opposite sides of the frame to each other, and protrude towards each other.

The locking members 382 are movably mounted onto the frame so that they may be moved away from each other, at least partially out of the opening. This reduces the extent that the locking members 382 protrude into the opening to allow the upper support ring 380 to be passed around and over the upper housing lip 180. Each locking member 382 is biased towards the centre of the opening so that, when released, the locking member 382 moves back into the opening and secures the upper support ring 380 over the upper housing lip 180. The biasing force may be provided by a spring, or any other form of resilient member.

Each locking member 382 is attached to a handle 385 that protrudes outwards from the frame. The handles 385 allow the user to lift the upper support ring 380 over the upper housing lip 180 whilst keeping their hands away from the production apparatus 100. Each handle 385 comprises a gripping section that allows the user to retract the locking members 382 from the opening, as discussed above.

FIG. 11 shows a detailed view of the front side of the carrier part of the surgical guide carrier. The carrier part 310 comprises a coupling portion 330 located on the front side of the rotatable portion 320. The coupling portion 330 is configured to receive and releasably couple to a mouldable material carrier.

The coupling portion 330 comprises a u-shaped housing comprising two side walls connected via a back wall. The side walls and back walls protrude from the front side of the carrier part 310. The side walls run parallel to each other. Each side wall comprises an upper lip that protrudes towards the opposite side wall. The side walls and upper lips therefore form opposing channels into which a corresponding section of the mouldable material carrier may be inserted. The upper lips are received into corresponding channels in the mouldable material carrier to prevent the mouldable material carrier from falling out of the coupling portion 330 without passing along the channels of the coupling portion 330.

The coupling portion 330 comprises a locking mechanism for securing the mouldable material carrier in place within the channels. The locking mechanism comprises a pair of locking members 332, each protruding into a corresponding channel of the coupling portion 330. The two locking members 332 are connected to a release button 334. The locking mechanism is configured to bias the locking members 332 towards an upward position extending into the channels, towards the upper lips. The locking members 332 may be urged at least partially out of the channels through the depression of the release button 334. This reduces the extent that the locking members 332 protrude into the channels thereby allowing the mouldable material carrier to be inserted or removed from the coupling portion 330.

Each locking member 332 comprises a sloped face facing towards an entrance of the coupling portion at entrances of the channels. The sloped faces means that as the mouldable material carrier is urged into the coupling portion, along the channels, the locking members 332 are depressed to allow the mouldable material carrier to be fully inserted into position. When the mouldable material carrier is fully inserted into the coupling portion 330, the locking members 332 are received into corresponding cavities in the mouldable material carrier to secure the mouldable material carrier in place.

The carrier part 310 comprises a coding element 350. Much like the coding element of the cutting attachment 200, this coding element 350 includes an indication of one or more properties of the carrier attachment 300. This indicates a type of the carrier attachment 300 to allow the production apparatus 100 to determine whether the correct carrier attachment 300 has been fitted. Different types of carrier attachment 300 may include different sizes or shapes of coupling portion 330 for different sizes or shapes of surgical guide.

As with the coding element of the cutting attachment 200, the coding element of the carrier attachment 300 may be a radio-frequency identification (RFID) chip, a barcode, QR code, memory device (e.g. flash), or any other form of machine-readable media. For instance, the coding element may encode the type of cutting element via its physical shape, which may be read by the production apparatus via, for instance, an optical sensor, or a configuration of buttons.

The production apparatus 100 may be configured to activate or deactivate based on whether the correct type of carrier attachment 300 is loaded onto the production apparatus 100.

Figure 12:
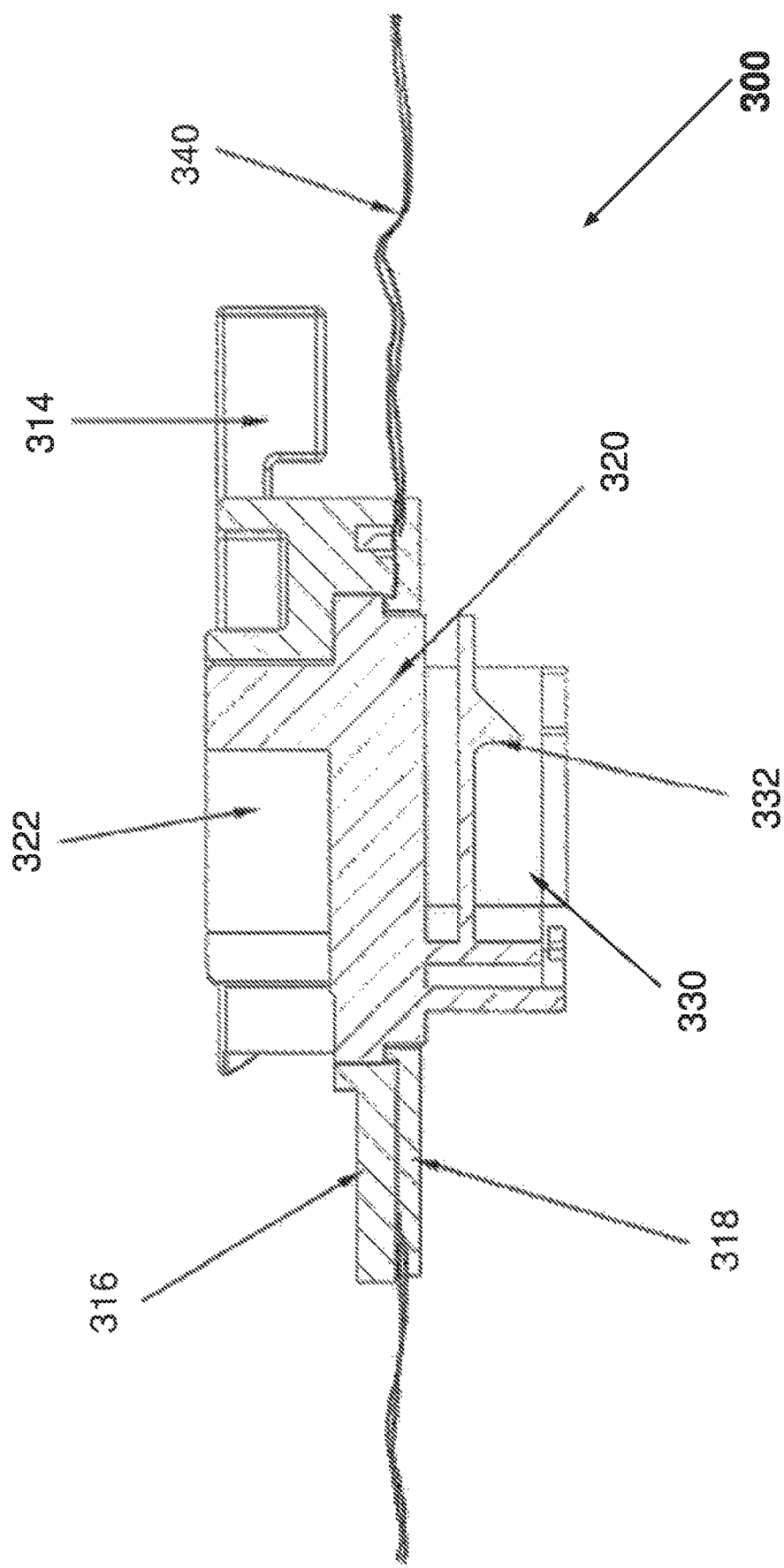
FIG. 12 shows a cross-sectional view of the surgical guide carrier.

FIG. 12 shows a cross-sectional view of the surgical guide carrier. The barrier drape 340 is secured between front 316 and back 318 housings of the carrier part 310. The rotatable part 320 passes through the carrier part 310 from the yaw axis keyway 322 to the coupling portion 330. The carrier part 310 is configured to allow the rotatable part 320 to be rotated within the carrier part 310 and about the yaw axis through a rotating force incident on the yaw axis keyway 322 so that the coupling portion 330 is rotated.

Figure 13:
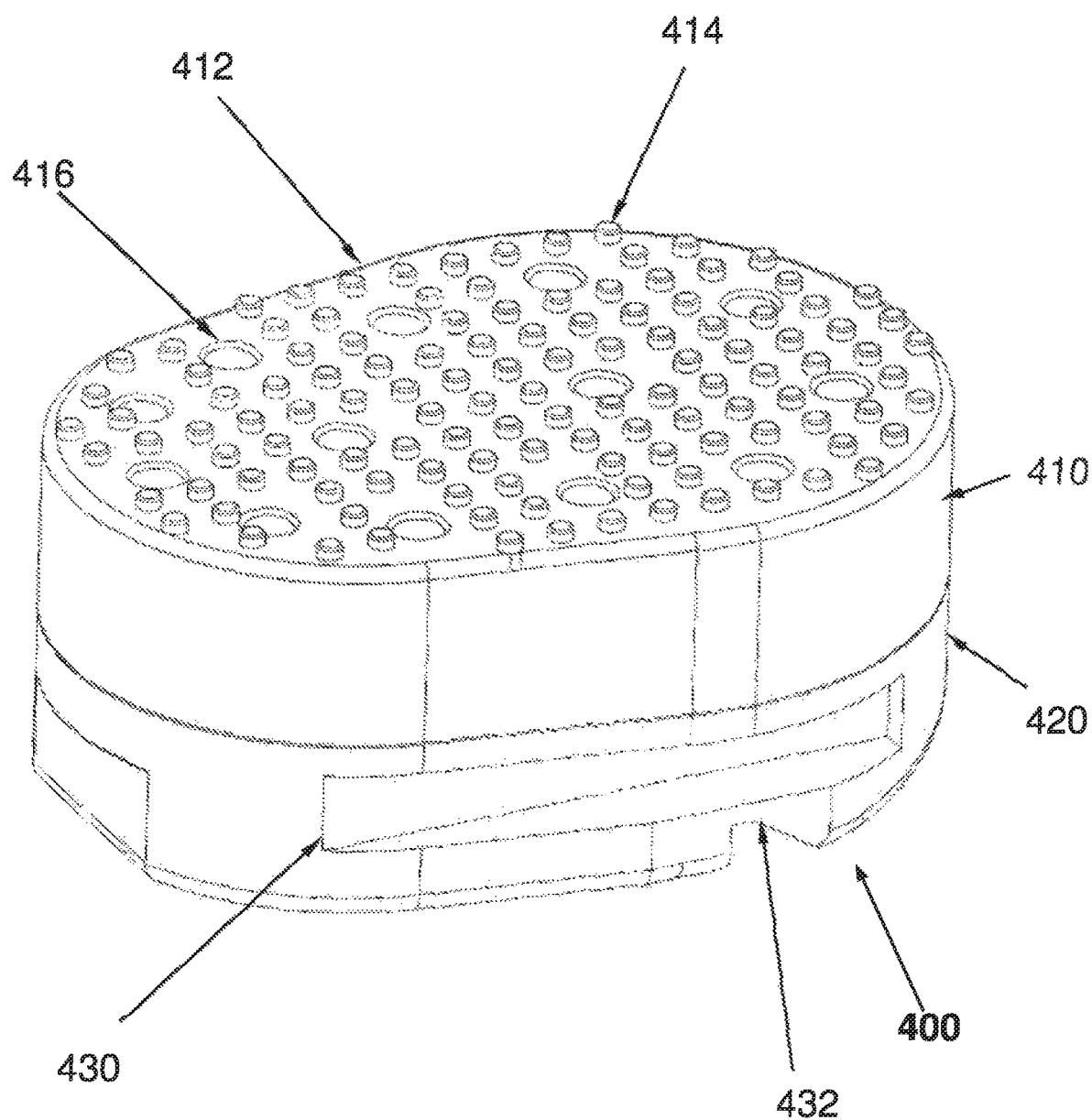
FIG. 13 shows a mouldable material carrier according to a first embodiment.

FIG. 13 shows a mouldable material carrier according to a first embodiment. The mouldable material carrier 400 is configured to receive mouldable material in such a way that the mouldable material is evenly distributed across a front surface 412 of the mouldable material carrier 400.

The mouldable material carrier 400 and the mouldable material may be used to form an impression of a surgical site. Once the mouldable material has hardened, the mouldable material carrier may be mounted onto the surgical guide carrier 300, which in turn is mounted upon the production apparatus 100. The production apparatus 100 can then scan the impression and modify the impression according to a surgical plan to produce a surgical guide.

Mouldable material carrier 400 is formed of front 410 and rear 420 parts that may be separately formed and subsequently bound together. The front and rear parts may be formed from injection-moulded plastic. The mouldable material carrier 400 has an entranceway formed in a rear face of the rear part 420 of the mouldable material carrier 400. The rear face is on the opposite side of the mouldable material carrier 400 to the front face 412. The entranceway is connected via internal passages to exit holes 416 in the front face 412. This means that the mouldable material carrier 400 is configured such that when mouldable material is injected into the entranceway, the mouldable material is urged through the mouldable material carrier 400 and out of the exit holes 416. The exit holes 416 are evenly spaced across the front face 412 of the mouldable material carrier 400. This helps to evenly distribute the mouldable material across the front face 412.

The front face 412 comprises a plurality of small protrusions 414 that are evenly distributed across the extent of the front face 412. These protrusions 414 provide purchase for the mouldable material by allowing the mouldable material to settle, and subsequently harden, around the protrusions. This means that the mouldable material is secured more firmly to the mouldable material carrier 400.

The rear part 420 comprises a coupling portion for coupling the mouldable material carrier 400 to the surgical guide carrier 300. The coupling portion comprises two channels 430 passing down the side of the rear part 420. The two channels 430 are formed to receive the upper lips of the coupling portion 330 of the surgical guide carrier 300. This allows the mouldable material carrier 400 to be slid into the channels of the surgical guide carrier 300. Two indentations for 432 are formed in the rear face of the mouldable material carrier 400 for receiving the locking members 332 of the coupling portion 330 of the surgical guide carrier 300. This allows the mouldable material carrier 400 to be locked in place within the coupling portion 330 of the surgical guide carrier 300.

A flat face 436 is located on a leading side of the mouldable material carrier 400. The flat face 436 runs perpendicular to the channels 430. The flat face 436 allows the mouldable material carrier 400 to sit square within the surgical guide carrier. This provides a secure fit to avoid the mouldable material carrier 400 moving within the surgical guide carrier 300.

FIG. 14 shows a perspective view of a syringe injecting mouldable material into the mouldable material carrier. As discussed above, an entranceway 424 is formed in the rear face 422 of the mouldable material carrier 400. The entranceway 424 is substantially frusto conical, having tapered walls such that its diameter reduces as it passes deeper into the mouldable material carrier. The tapered walls allow the conical tip of the syringe may to be fitted securely into the entranceway 424. This provides an interference fit around the syringe to prevent mouldable material from escaping out of the entranceway 424 as it is being urged into the mouldable material carrier 424. The tapered walls also help the user to position the syringe correctly to ensure effective transfer of the mouldable material into the mouldable material carrier 400.

FIG. 15 shows the internal structure of the mouldable material carrier. The mouldable material carrier 400 comprises a front part 410 and a rear part 420. The front part 410 comprises the front face 412 and a rear face 418 on the opposite side to the front face 412. The rear part 420 comprises the rear face 422 and a front face 428 on the opposite side to the rear face 422. When the mouldable material carrier 400 is assembled, the rear face 418 of the front part 410 is secured to the front face 428 of the rear part 420.

Interconnected channels 429 formed in the front face 428 of the rear part 420. The entranceway 424 in the rear face 422 of the rear part 420 passes through the rear part 420 and opens into the channels 429.

A corresponding set of channels 419 are formed in the rear face 418 of the front part 410. The channels 419 in the front part 410 into the exit holes 416 on the front face 412 of the front part 410.

Channels 419 and 429 are mirror images of each other. The channels 419 and 428 are in the form of one seven-pointed asterisk or star and one six-pointed asterisk or star. Each asterisk is linked to the other via one of its points/legs.

When the front 410 and rear 420 parts are combined, the two sets of channels 419, 429 combine to form tunnels within the mouldable element carrier 400. Mouldable material may therefore be injected into the entranceway 424 and be urged through the tunnels and out of the exit holes 416.

The entranceway 424 and the exit holes 460 are arranged to ensure an even distribution of mouldable material across the front face 412. Accordingly, the entranceway 424 is centrally located on the rear face 422. This leads to a longitudinally running tunnel that connects the entranceway to two central exit holes 416 that sit on either side of the entranceway 424. These two central exit holes 416 and the entranceway 424 all lie along a central axis of the mouldable material carrier 400. One of the central exit holes 416 is surrounded by six outer exit holes 416, each linked to the corresponding central exit hole 416. The other of these central exit holes 416 is surrounded by five outer exit holes 416, each linked to the corresponding central exit hole 416. The star formation of the tunnels helps to ensure the even distribution of mouldable material across the front surface 412.

It should be noted that the precise number of channels and holes may vary between embodiments depending on the size of the mouldable material carrier.

Figure 16:
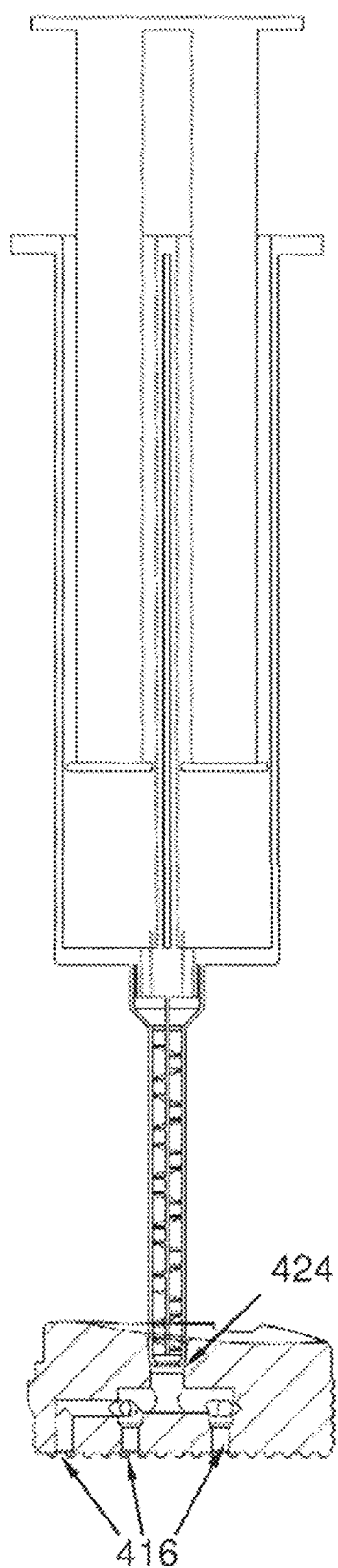
FIG. 16 shows a cross-sectional view of a syringe injecting mouldable material into the mouldable material carrier.

FIG. 16 shows a cross-sectional view of a syringe injecting mouldable material into the mouldable material carrier. The syringe fits into a tapered channel that forms part of the entranceway. The tapered walls prevent the tip of the syringe from being inserted into the longitudinally running tunnel that connects the entranceway to the central exit holes 416. The tapered walls also provide a seal around the syringe to prevent mouldable material from escaping out of the entranceway 424 as mouldable material is being injected into the mouldable material carrier 424.

When mouldable material is injected into the entranceway 424 it passes through the internal tunnels and is urged out of the exit holes 416 to be distributed across the front face 412 of the mouldable material carrier.

The mouldable material carrier described with reference to FIGS. 13-16 is only one embodiment. There are many different arrangements that can allow the mouldable material to be distributed evenly across the surface of the mouldable material holder. For instance, a second embodiment shall be described with reference to FIGS. 17-24.

Figure 17:
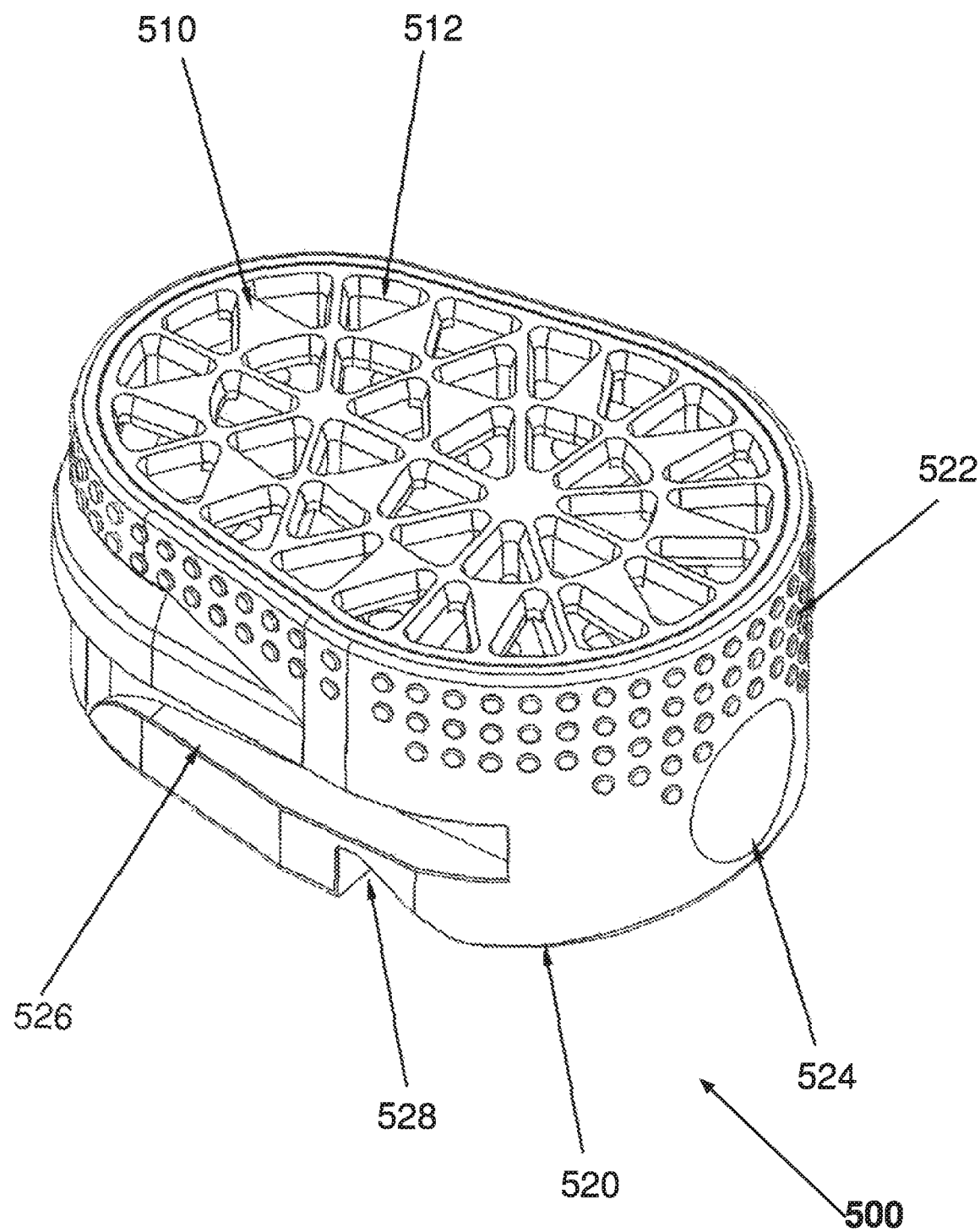
FIG. 17 shows a mouldable material carrier according to a second embodiment.

FIG. 17 shows a mouldable material carrier according to a second embodiment. The mouldable material carrier 500 of the second embodiment is similar to that of the first embodiment; however, it includes a number of splitting stages for evenly splitting the mouldable material to distribute it across the front surface.

The mouldable material carrier 500 comprises a front section 510 and a back section 520. The front section 510 fits within a cavity within the back section 520. A number of openings 512 pass through the front section 510, acting as extra holes for the mouldable material. In the present embodiment, the openings 512 are triangular.

The rear section 520 forms the outer housing of the mouldable material carrier 500. The rear section 520 is substantially cup-shaped, forming an internal cavity into which first and second splitters, and the front section 510, may be received. The rear section 520 comprises a number of protrusions 522 distributed around the outer surface of sidewalls of the rear section 520 to provide additional grip for the user when holding the mouldable material carrier 500.

An entranceway 524 is formed in the sidewall at one end of the mouldable material carrier 500. This entranceway 524 is an opening that serves a similar function to the entranceway shown in FIGS. 13-16. The entranceway 524 is connected to the internal cavity so that, when mouldable material is inserted into the entranceway 524, it passes into the internal cavity, is split by the first and second splitters, and is urged out of the openings 512 in the front section 510 to evenly distribute the mouldable material across a front surface of the front section 510.

By locating the entranceway 524 on a sidewall, rather than the rear of the mouldable material carrier 500, mouldable material may be more easily syringed into the entranceway when the user is holding the mouldable material carrier 500.

Coupling features are located on the rear of the mouldable material carrier 500. These coupling features are similar to those provided in the embodiment of FIGS. 13-16. Two coupling channels 526 are formed in the sidewalls. The coupling channels 526 are located on opposite sides of the mouldable material carrier 500 to each other. The coupling channels 526 past longitudinally along the sidewalls, parallel to the front and rear surfaces. This allows the mouldable material carrier 500 to be slid into the coupling section of the surgical guide carrier 300. An indentation 528 is formed in the rear of the rear section for receiving the locking members 332 of the coupling portion 330 of the surgical guide carrier 300. This allows the mouldable material carrier 400 to be locked in place within the coupling portion 330 of the surgical guide carrier 300.

Figure 18:
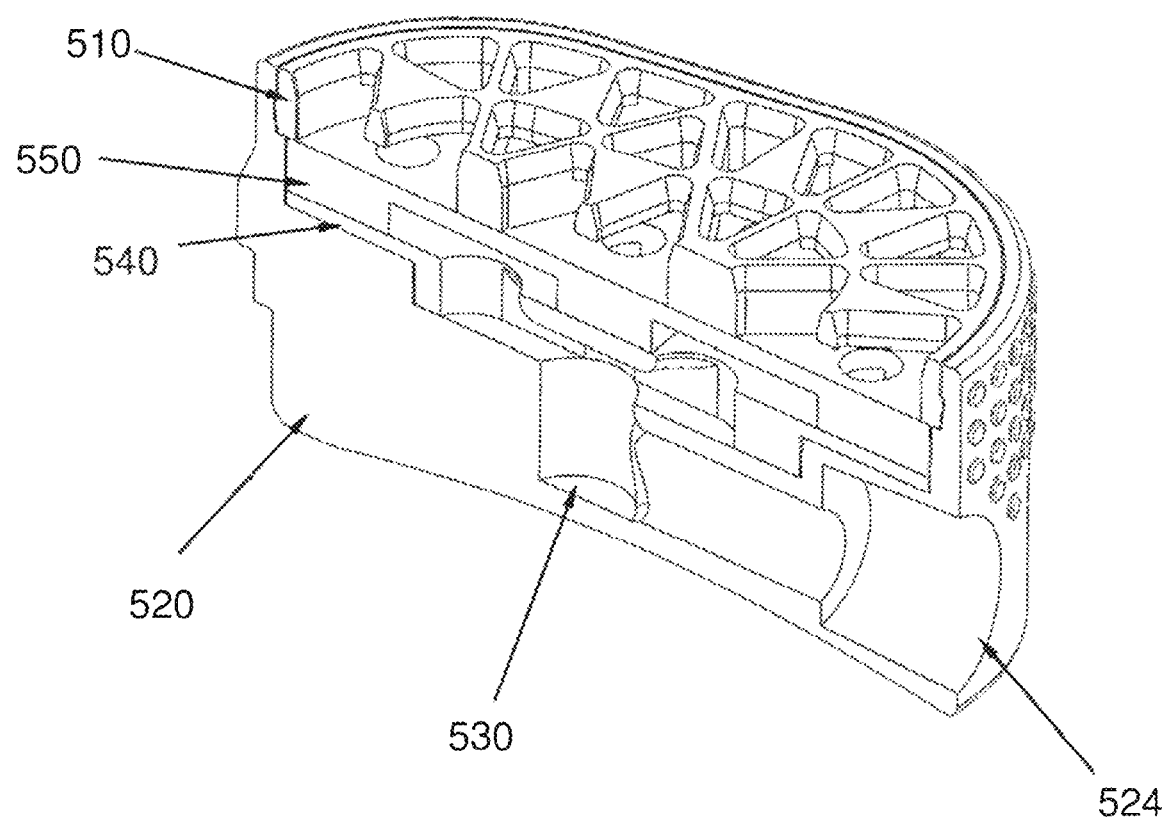
FIG. 18 shows a cross-sectional view of the mouldable material carrier of FIG. 17.

FIG. 18 shows a cross-sectional view of the mouldable material carrier of FIG. 17. The rear section 520 comprises a base and a peripheral side wall protruding from the base and encircling a cavity. The entranceway 524 is formed in the side of the rear section 520 and passes into the base. The entranceway 524 is substantially frusto conical, narrowing as it passes into the base. The entranceway 524 is connected to an internal tunnel 530 that passes into the centre of the base and opens at a central opening within the cavity.

A first splitter 540 is located within the cavity, above the central opening. This serves to divide mouldable material that exits the central opening in two. A second splitter 550 is located within the cavity, above the first splitter 540. This serves to further divide the mouldable material. The front section 510 is located in the cavity, above the second splitter 550. The front section 510 is secured within the cavity via an interference fit with a coupling section of the rear section.

When the front section 510 is secured within the cavity, the first 540 and second 550 splitters are also retained within the cavity.

Figure 19A:
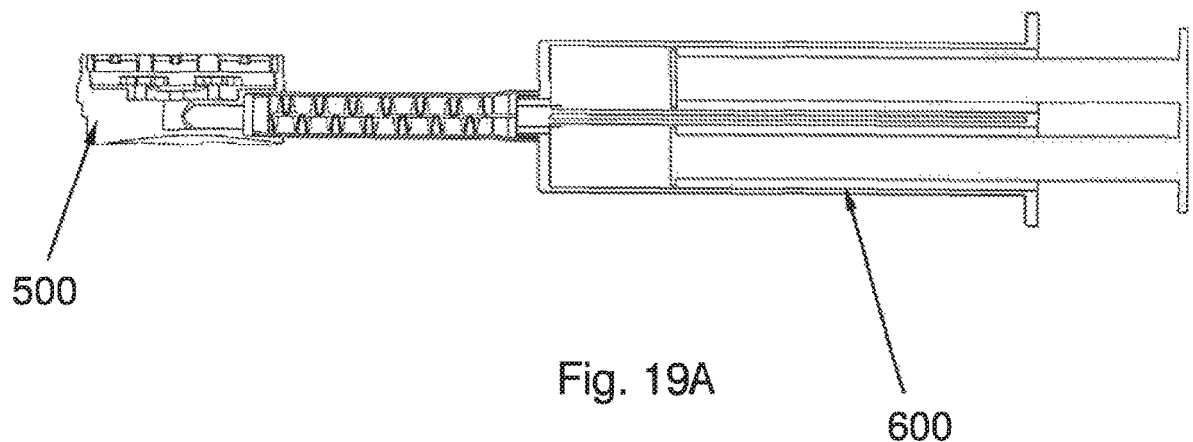
FIGS. 19A and 19B show a cross-sectional view and a perspective view, respectively, of a syringe injecting mouldable material into the mouldable material carrier of FIG. 17.
Figure 19B:
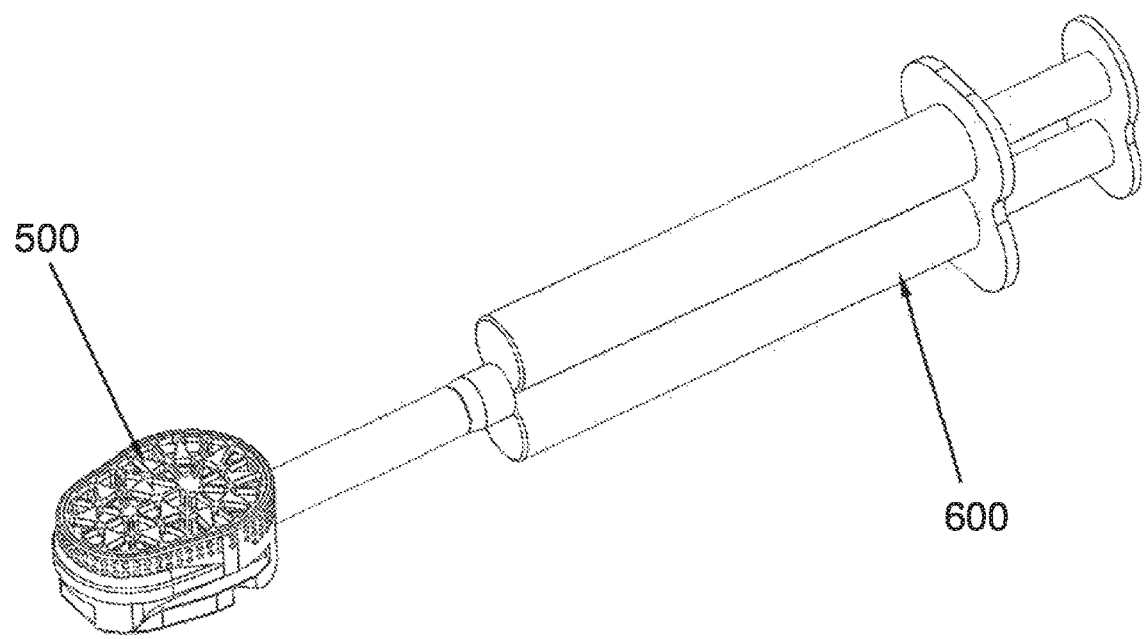

FIGS. 19A and 19B show a cross-sectional view and a perspective view, respectively, of a syringe injecting mouldable material into the mouldable material carrier of FIG. 17. As with the mouldable material carrier of FIG. 14, mouldable material may be injected into the carrier via a syringe 600.

A controlled amount of mouldable material is provided in the syringe (the syringe is provide pre-filled with the correct amount of material for the type of surgical guide). This ensures that the appropriate amount of material is distributed across the mouldable material carrier 500.

When mouldable material is urged into the entranceway 524, it is urged into the cavity and split evenly via the first 540 and second 550 splitters and the openings 512 in the front section 510. Mouldable material is urged out of the openings 512 to provide an even distribution of mouldable material across the front face of the mouldable material carrier 500.

Figure 20:
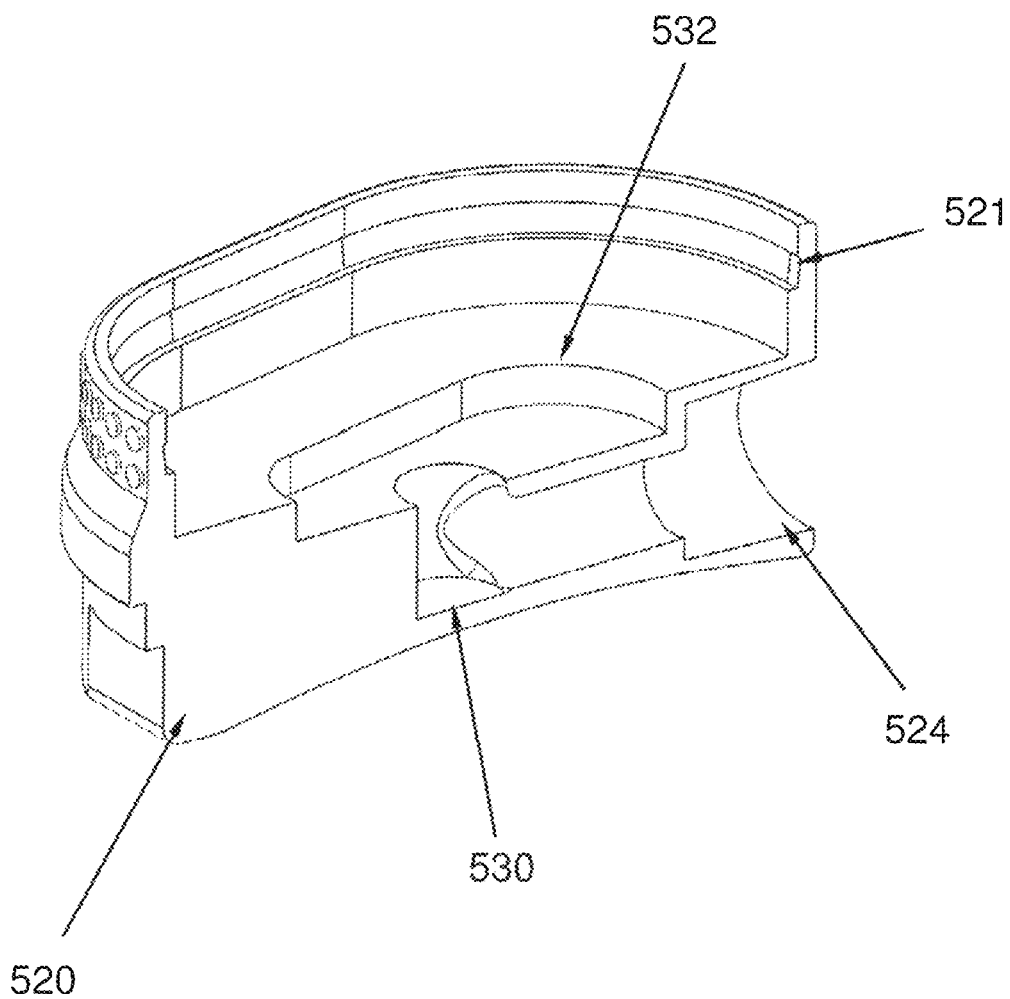
FIG. 20 shows a cross-sectional view of a rear section of the mouldable material carrier of FIG. 17.

FIG. 20 shows a cross-sectional view of a rear section of the mouldable material carrier of FIG. 17. As discussed above, the entranceway 524 in the side of the rear section 520 is connected to an internal tunnel 530 that in turn is connected to a central opening that opens into the cavity.

A central indentation 532 is located in the base of the cavity for receiving part of the first splitter 540.

A groove 521 is formed on the inner face of the sidewall, running around the sidewall, parallel to the base of the cavity. This provides a coupling portion into which the front section 510 may be secured, for instance, via a snap fit.

Figure 21:
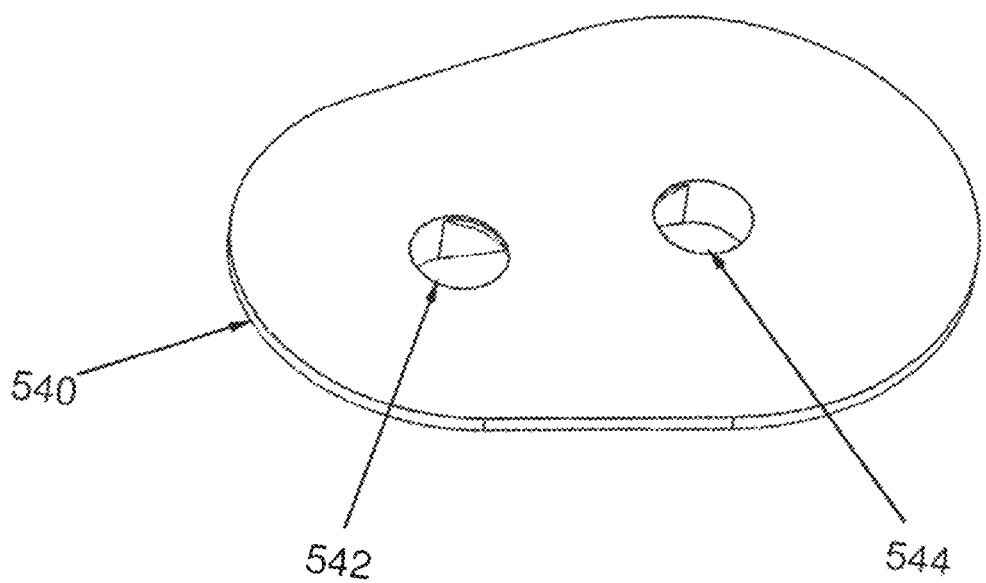
FIG. 21 shows a first stage splitter of the mouldable material carrier of FIG. 17.

FIG. 21 shows a first stage splitter of the mouldable material carrier of FIG. 17. The first stage splitter 540 splits the mouldable material that exits the central opening into two portions.

First 542 and second 544 openings are formed in the first stage splitter 540, passing from a rear side to a front side of the first stage splitter 540. The two openings 542, 544 are located along a central axis of the mouldable material carrier, but are separated from each other along the central axis. The two openings 542, 544 are substantially evenly spaced across the length of the mouldable material carrier.

The front side of the first stage splitter 540 is substantially flat. The rear side of the first stage splitter 540 comprises a splitting portion that protrudes from the base of the first stage splitter 540. This splitting portion fits within the central cavity 532. The splitting portion comprises a first cavity located in the centre of the splitting portion 540 and opening onto the rear of the splitting portion 540. The first cavity forms a channel between the first 542 and second 544 openings. The two openings 542, 544 open into the channel.

When the first stage splitter 540 is positioned within the cavity of the rear section 520, the channel is located above the central opening in the rear section 520. The first 542 and second 544 openings are offset from the central opening and do not overlap the central opening. This means that when mouldable material is urged out of the central opening, it is urged against the base of the first stage splitter 540 and is therefore forced to pass down the channel, towards the first 542 and second 544 openings.

The first 542 and second 544 openings are equidistant from the central opening and have equivalent cross sections. This means that the mouldable material is evenly split between the first 542 and second 544 openings.

Figures 22A, 22B, 22C:
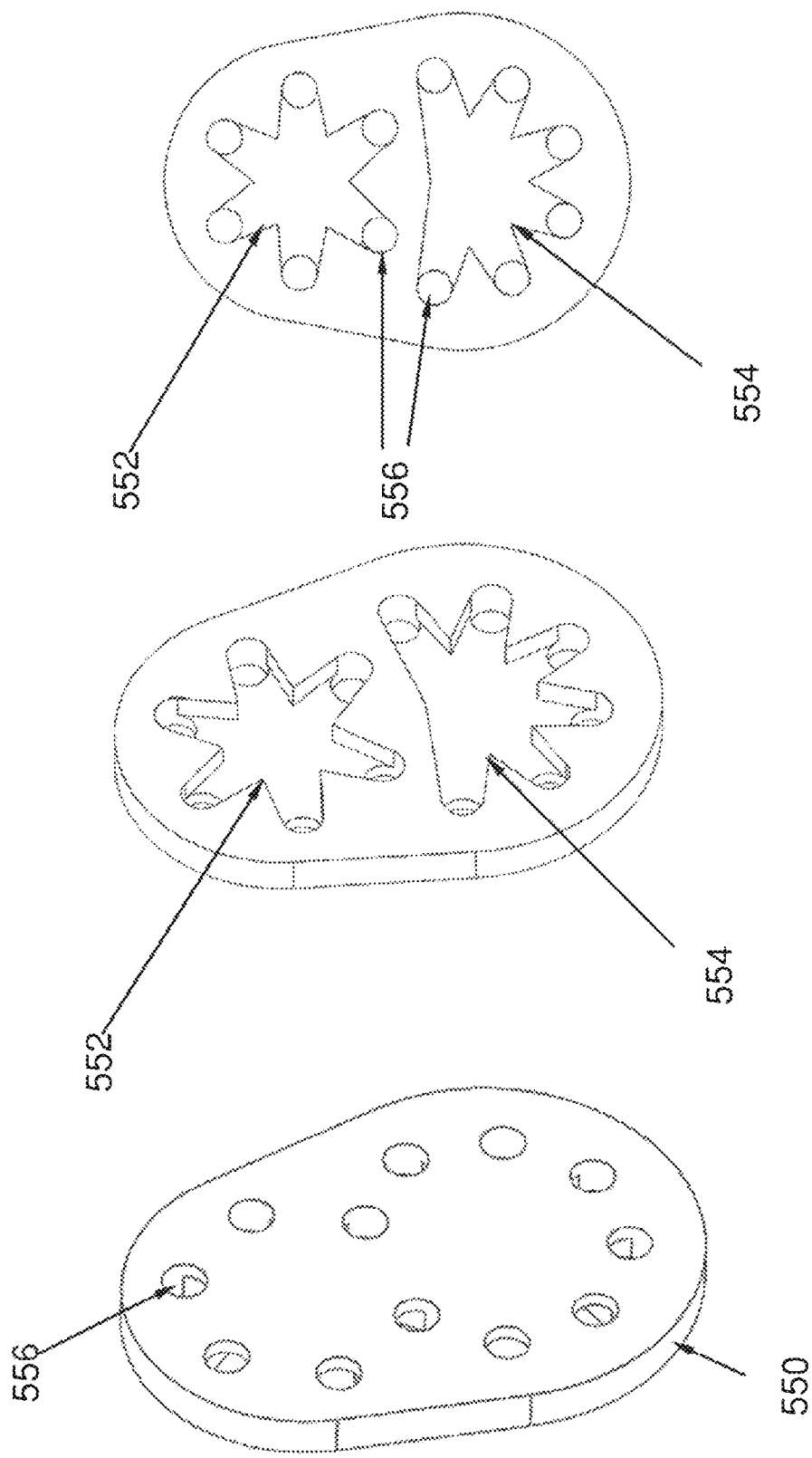
FIG. 22A shows a perspective view of a front side of a second stage splitter of the mouldable material carrier of FIG. 17.
FIG. 22B shows a perspective view of a rear side of the second stage splitter.
FIG. 22C shows a plan view of the rear side of the second stage splitter.

FIG. 22A shows a perspective view of the front side of a second stage splitter of the mouldable material carrier of FIG. 17. The second stage splitter 550 splits each of the two portions of mouldable material from the first stage splitter 540 into six corresponding portions. The second stage splitter 550 therefore splits the mouldable material into a total of twelve portions.

The second stage splitter 550 is substantially planar and comprises twelve openings 556 that pass from a front face of the second stage splitter 550 to a rear face of the second stage splitter 550. The twelve openings 556 are arranged across the front face of the second stage splitter 550 in the form of two circles that intersect at a centre point of the second stage splitter 550. Each of the twelve openings 556 has substantially the same cross-section as the other openings 556.

When the second stage splitter 550 is placed over the first stage splitter 550, the two circles are centred on the first 542 and second 544 openings of the first stage splitter 540.

FIG. 22B shows a perspective view of the rear side of the second stage splitter. The second stage splitter 540 is divided into first 552 and second 554 splitting sections. Each of the splitting sections 552, 554 comprises six channels connected to a respective six of the twelve openings 556. The sixth channels all meet at the centre of the splitting section. The two splitting sections 552, 554 are not connected to each other.

FIG. 22C shows a plan view of the rear side of the second stage splitter. The first splitting section 552 is in the shape of a six-pointed star. The second splitting section 554 is in the shape of an eight-pointed star, with two adjacent points having been removed. The first splitting portion fits partially within the gap in the second splitting section where the two adjacent points are missing.

Each splitting section 552, 554 has a central point from which its respective channels radiate away. For each splitting section 552, the respective openings 556 are located an equivalent distance away from the respective central point. In other words, each splitting section 552, 554 comprises channels of equal length. This ensures that the mouldable material within each splitting section is split evenly.

When the second stage splitter 550 is placed above the first stage splitter 540, the central points are located over the first 542 and second 544 openings of the first stage splitter 540.

When mouldable material is urged out of the first 542 and second 544 openings, it is urged against the rear face of the second stage splitter 550. The mouldable material is therefore urged along each of the channels and urged out of the corresponding openings 556, thereby splitting the mouldable material into twelve portions.

As the openings have the same cross-section, and for each splitting section are located the same distance away from the central point, the mouldable material is split substantially evenly between the twelve openings 556.

Figure 23A:
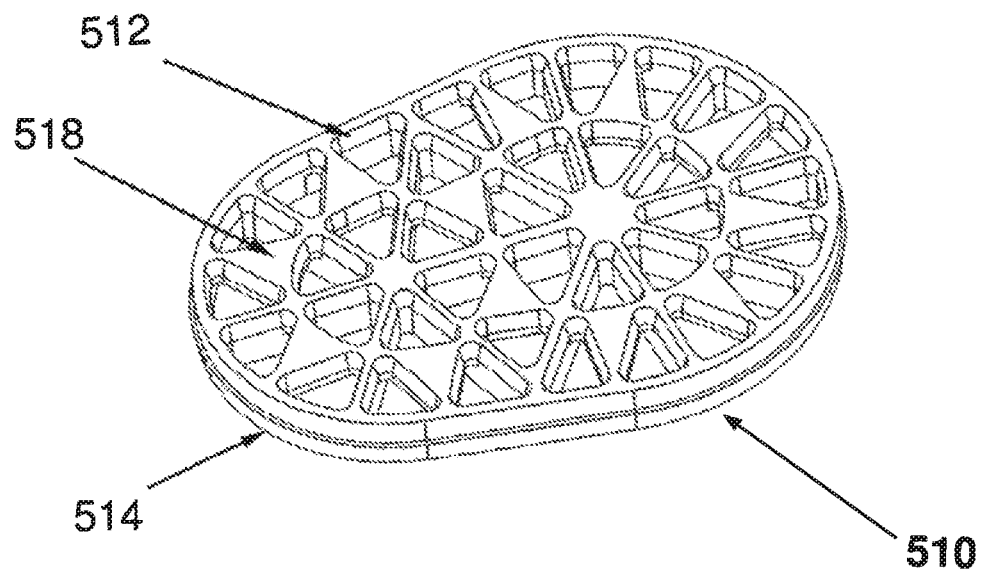
FIG. 23A shows a front side of a front section of the mouldable material carrier of FIG. 17.

FIG. 23A shows a front side of a front part of the mouldable material carrier of FIG. 17. The front part 510 of the mouldable material carrier is configured to split each of the portions of mouldable material received from the second stage splitter 550 into three equal portions. Accordingly, the front part 510 forms a third stage splitter to split the mouldable material into a total of thirty six portions.

A lip 514 is located on the outer edge of the front part 510. The lip 514 is configured to be received within the channel 521 in the sidewall of the rear portion 520 of the mouldable material carrier 500 to secure the front part 510 within the rear part 520.

Figure 23B:
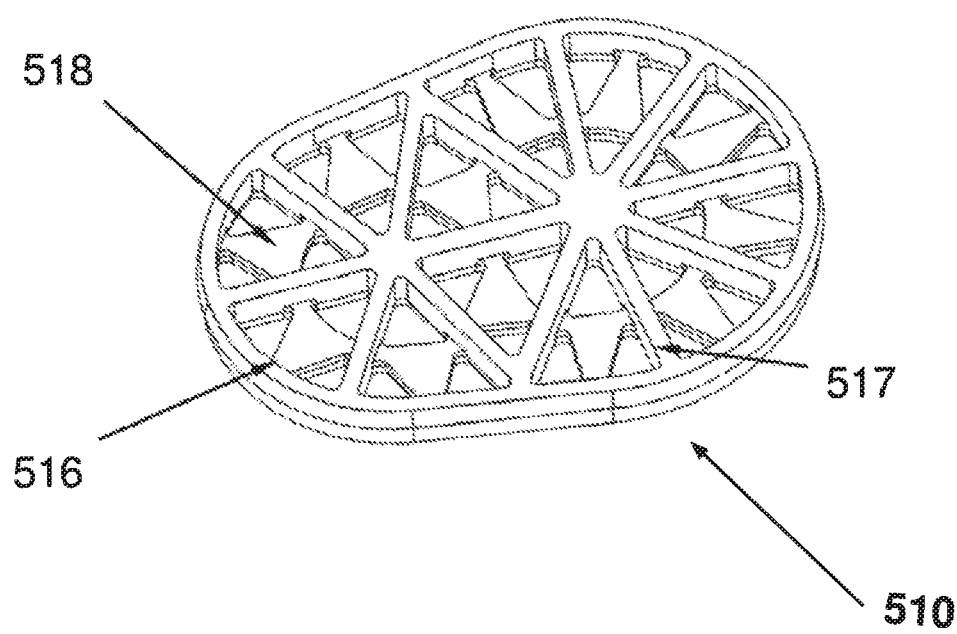
FIG. 23B shows a rear side of the front section.

FIG. 23B shows a rear side of the front section. Twelve triangular cavities 516 are formed on the rear side; one for each opening on the second stage splitter 550. As with the openings 556 on the second stage splitter 550, the triangular cavities 516 are arranged in a star pattern.

The rear side of the front section 510 is effectively subdivided by number of spokes 517. Two sets of spokes radiate out from two corresponding central points. This divides the rear side into twelve openings 516 of equal cross-section. When the front section 510 is positioned over the second stage splitter 550, the triangular cavities 516 are centred over the corresponding openings 556 in the second stage splitter 550.

Figure 24:
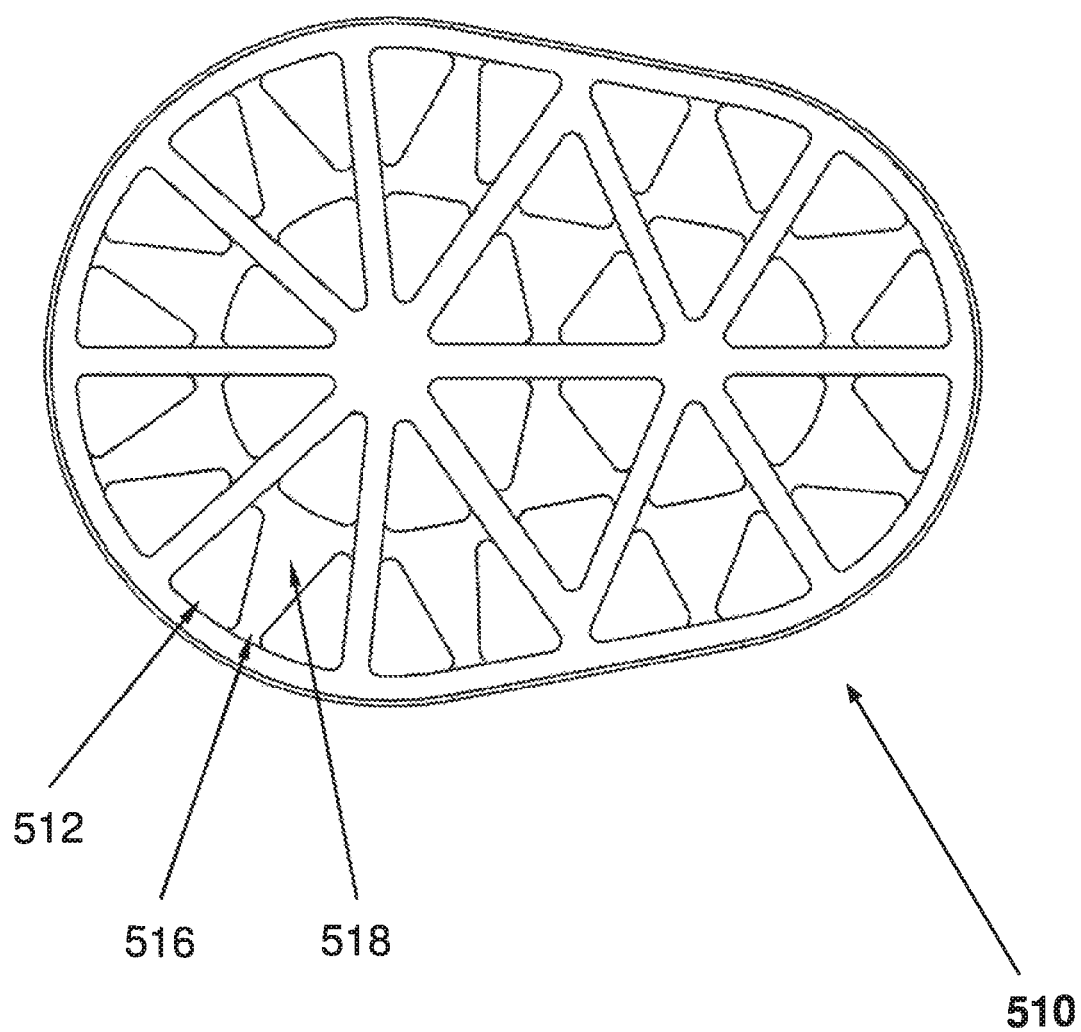
FIG. 24 shows a plan view of the rear side of the front section.

FIG. 24 shows a plan view of the rear side of the front section. Each triangular cavity 516 a triangular cross-section and is open on the rear face of the front section 510. Each triangular cavity 516 is connected to three corresponding triangular openings 512 on the front side (front face) of the front section 510. Each of the three triangular openings 512 opens onto a respective corner of the corresponding triangular cavity 516.

The three triangular openings 512 are separated by a splitting wall 518 that is centred on the cavity 516 and forms an upper roof of the cavity 516. In this case the splitting wall 518 is triangular. When the front section 510 is positioned above the second stage splitter 550, the splitting wall 518 passes over the entirety of the corresponding opening 556 in the second stage splitter 550. This prevents mouldable material from exiting the opening 556 without some deflection. When mouldable material is urged out of the opening 556, it is urged against the splitting wall 518 and deflected to one of the three triangular openings 512. This ensures that the triangular cavity 516 is filled with mouldable material before mouldable material is extruded out of the triangular openings 512. This therefore provides an even distribution of mouldable material.

Each of the triangular openings 512 has the same area cross-section and is positioned the same distance away from the centre point for the corresponding triangular cavity 516. In addition, the triangular openings 512 are substantially evenly distributed across the front face of the front section 510. Accordingly, the front section 510 splits the mouldable material evenly to provide an even distribution of mouldable material across the front face of the front section 510.

Whilst the above embodiments describe specific arrangements in which mouldable material may be split into a specific number of portions (thirteen portions in the first embodiment and thirty six portions in the second embodiment), it will be appreciated that the number of portions may be altered depending on the size of the mouldable material carrier and the function that it serves. Additional or fewer splitting stages may be implemented depending on the number of portions that may need to be provided.

Equally, whilst the above embodiment describes triangular openings and triangular cavities, the shapes of the openings and cavities may be adapted for the specific geometries of the mouldable material carrier.

In addition, whilst the above embodiments aim to distribute mouldable material evenly, it will be appreciated that alternative embodiments may arrange the splitters or openings in the front surface of the mouldable material carrier to provide a larger volume of mouldable material to the centre of the front surface than to the periphery. This can be useful for situations where the mould is to fit within a socket and therefore is expected to be substantially dome shaped.

Furthermore, whilst the mouldable material carrier has been described as being formed of multiple parts that may be connected together, the mouldable material carrier may be manufactured via a variety of methods, including additive manufacturing, and therefore may be formed as a single part or of separate parts.

Multiple parts of an overall system have been described herein. These parts combine together to provide an overall system for producing a surgical guide. These parts may be provided separately or together. The process of producing a surgical guide from an impression of a surgical site is described below.

Figure 25B:
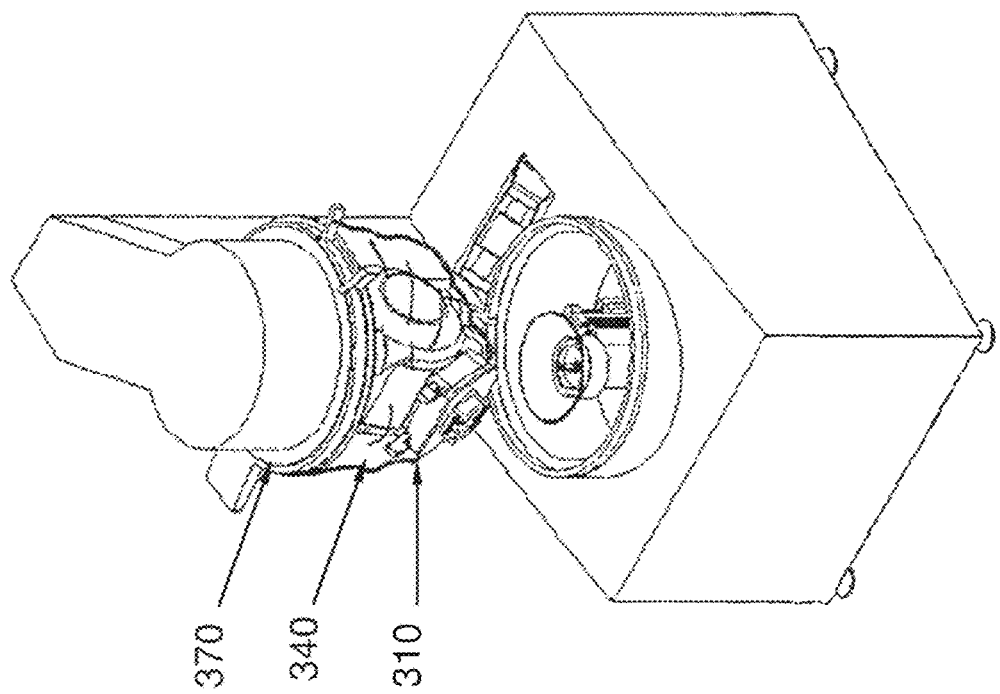
FIG. 25B shows a second step in a surgical guide production procedure according to an embodiment.
Figure 25A:
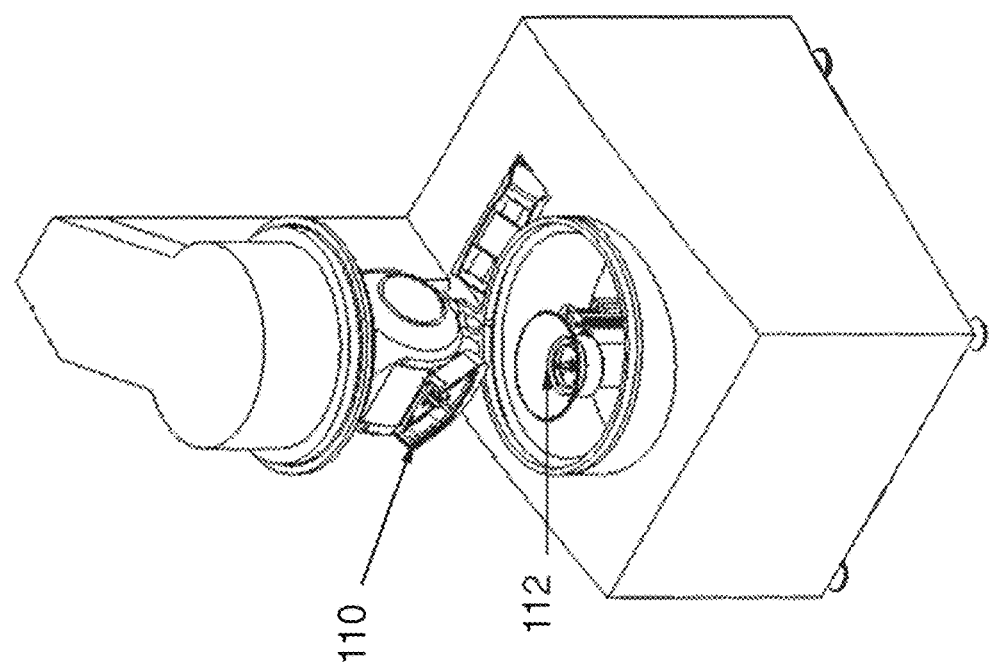
FIG. 25A shows a first step in a surgical guide production procedure according to an embodiment.

FIG. 25A shows a first step in a surgical guide production procedure according to an embodiment. The driven support ring 160 is lowered to its retracted position. The mounting point 110 for the surgical guide carrier 300 is tilted forwards via the gimbal 140 to allow the user to access the mounting point 110.

FIG. 25B shows a second step in a surgical guide production procedure according to an embodiment. The carrier part 310 of the surgical guide carrier 300 is secured to the mounting point 110 by slotting the carrier part 310 into the mount. This is done with the user's hand inserted into the barrier drape 340 of the surgical guide carrier 300 to provide a sterile barrier against contamination from the non-sterilised portions of the production apparatus 100 (e.g. the gimbal 140). If the production apparatus registers that the incorrect surgical guide carrier 300 has been used, the production apparatus may deactivate and/or issue a warning to the user.

The upper support ring 370 is expanded to allow it to fit over the upper housing lip 180 of the production apparatus 100. The upper support ring 370 is then lifted over the upper housing lip 180 and allowed to contract; thereby securing the barrier drape 340 over the upper housing lip 180 two encase the gimbal 140.

Figure 25D:
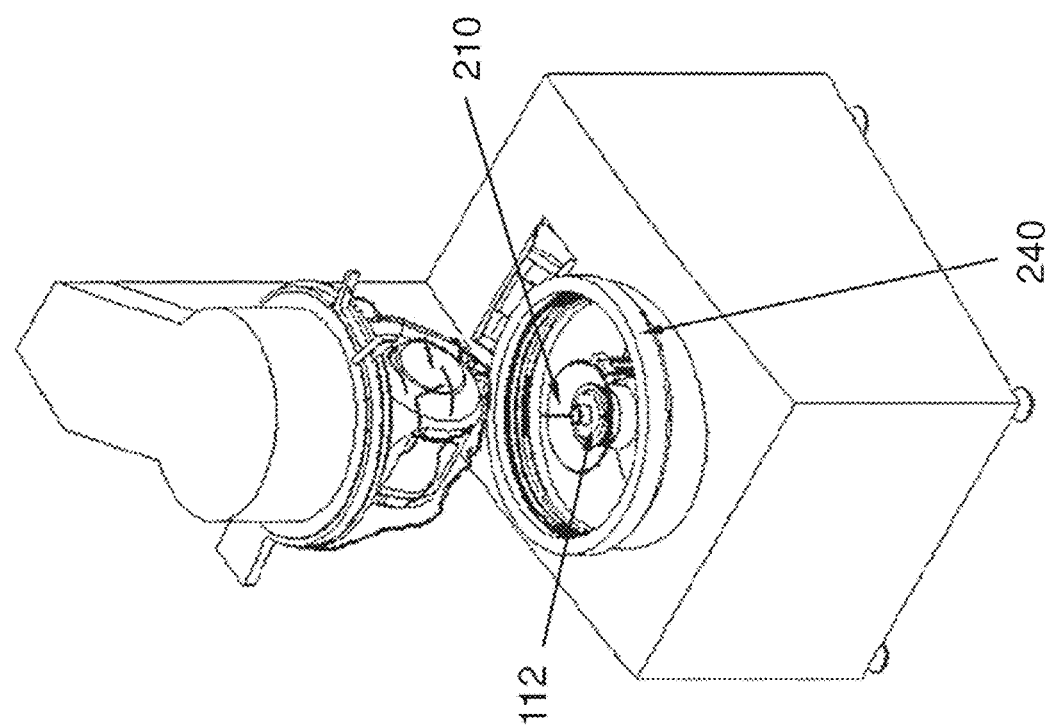
FIG. 25D shows a fourth step in a surgical guide production procedure according to an embodiment.
Figure 25C:
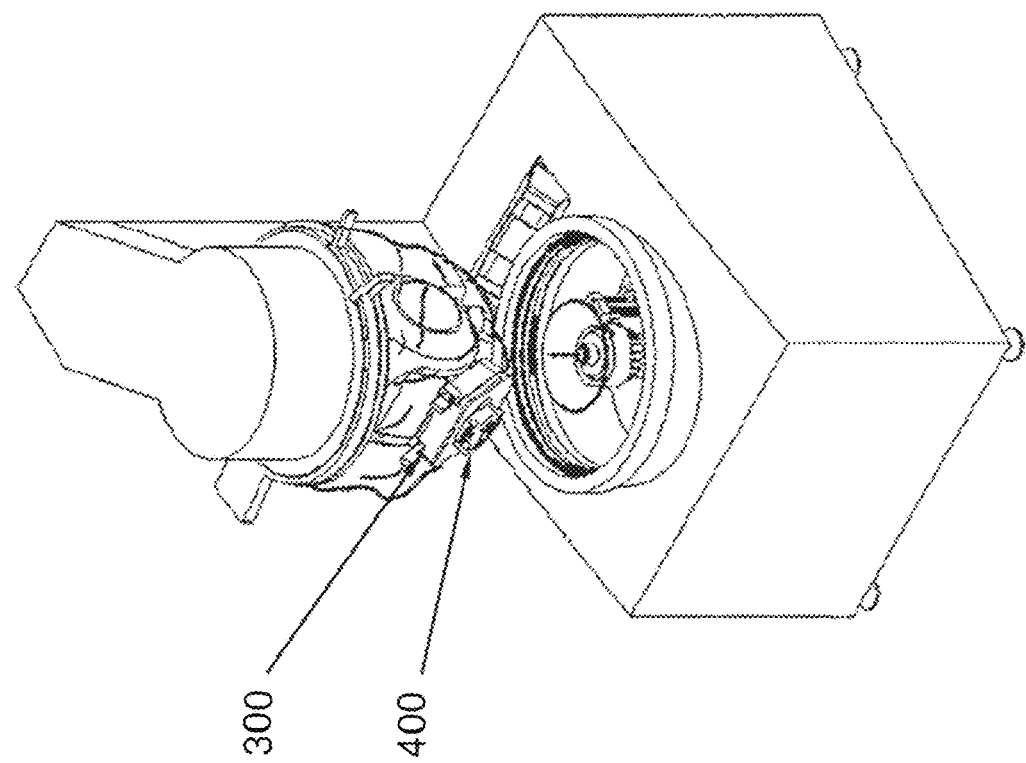
FIG. 25C shows a third step in a surgical guide production procedure according to an embodiment.

FIG. 25C shows a third step in a surgical guide production procedure according to an embodiment. The gimbal 140 is then tilted to a backwards position to move the mounting point 110 and the surgical guide carrier 300 out of the way of the user so that the cutting attachment 200 may be fitted to the production apparatus 100.

The cutting element 210 is coupled to the coupling section 112 of the production apparatus 100 and the upper support ring 240 of the cutting attachment 200 is secured over the driven support ring 160. If the production apparatus registers that the incorrect cutting attachment 200 has been used, the production apparatus may deactivate and/or issue a warning to the user.

FIG. 25D shows a fourth step in a surgical guide production procedure according to an embodiment. The gimbal 140 is tilted forwards to allow the user to access the surgical guide carrier 300. After an impression of a surgical site has been taken using mouldable material deposited onto the mouldable material carrier 400, the mouldable material carrier 400 is mounted onto the surgical guide carrier 300.

Figure 25F:
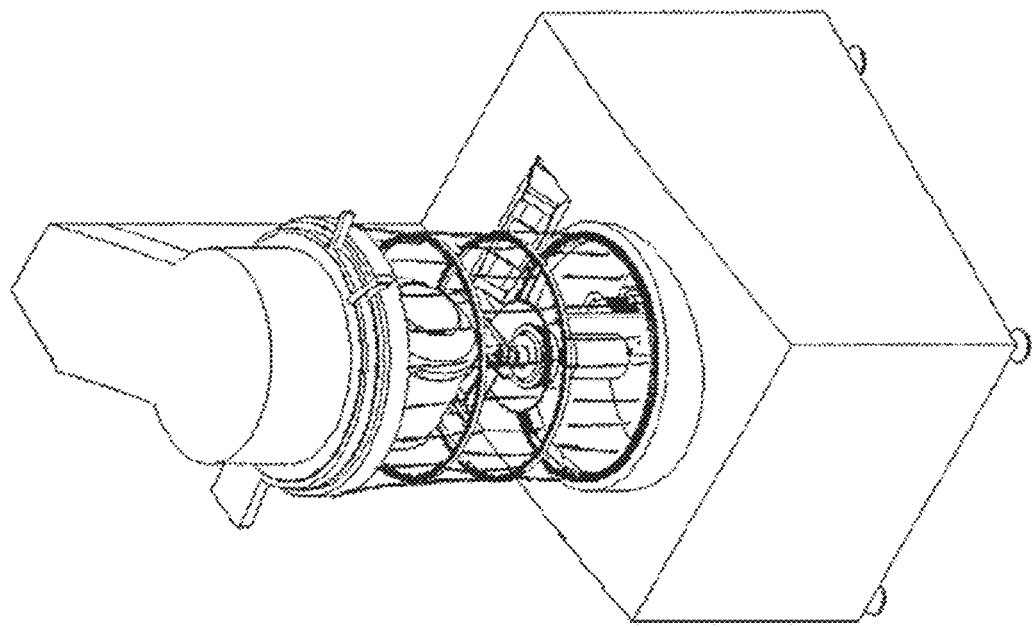
FIG. 25F shows a sixth step in a surgical guide production procedure according to an embodiment.
Figure 25E:
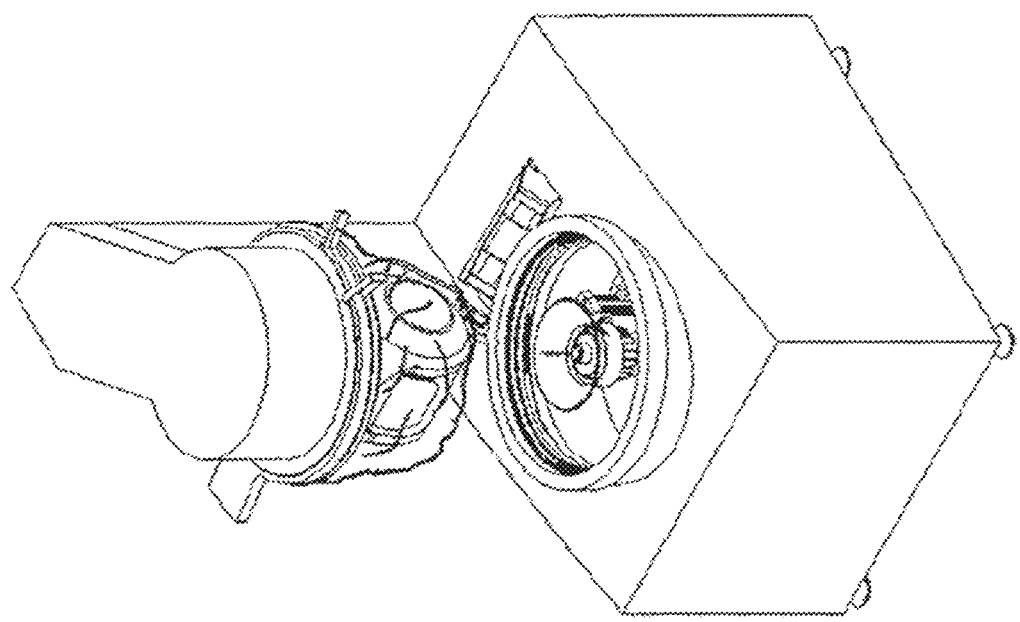
FIG. 25E shows a fifth step in a surgical guide production procedure according to an embodiment.

FIG. 25E shows a fifth step in a surgical guide production procedure according to an embodiment. The gimbal 140 is tilted backwards, towards the scanner 150. The scanner 150 takes a scan of the surface of the impression.

The production apparatus 100 then registers the surface of the impression to anatomical features of the patient, shown in a medical scan of the patient. The production apparatus 100 then determines the appropriate operations to modify the impression to produce a surgical guide in accordance with a predefined surgical plan.

FIG. 25F shows a sixth step in a surgical guide production procedure according to an embodiment. The driven support ring 160 is raised to raise the barrier drape 220 of the cutting attachment 200 around the cutting area to seal off the cutting area from the surrounding area.

The impression is then rotated via the rotation mechanism to the correct tilt and yaw angles and the cutting attachment 210 is moved to the correct position in the x, y and z axes for the first surgical guide hole to be produced. The cutting attachment 210 (in this case a drill) is driven into the impression of the surgical site to form a guide hole. This process is repeated until a surgical guide with the required number of guide holes is created. The driven support ring 160 is then lowered so that the surgical guide can be removed from the surgical guide carrier 300.

As the coupling portion 112 for the cutting attachment 210 is located below the mounting point 110 for the carrier part 310, debris from the impression during the modification falls away from the impression and is collected within the barrier drape 220 of the cutting attachment 200. When the operation has been completed, this debris may be easily collected within barrier drape 220 by the user as the cutting attachment 200 is removed from the production apparatus 100.

Embodiments described herein include a surgical guide production apparatus and various attachments for surgical guide production apparatus that help to allow the production apparatus to be utilised within a sterile environment such as an operating theatre without compromising the sterile environment.

The inclusion of respective integrated barrier drapes in a cutting attachment and a surgical guide carrier allows these attachments to be loaded onto the production apparatus with the barrier drape covering the user's hand. This means that the production apparatus itself does not need to be sterilised, thereby reducing the cost of operating the production apparatus and reducing the turnaround time after surgery.

By providing an elongated tubular barrier drape as part of a cutting attachment this barrier drape may be positioned around the cutting area to seal off the cutting area from the outside. This prevents debris from the cutting process from escaping the production apparatus and contaminating the surrounding area. As the cutting attachment is loaded onto the production apparatus below the surgical guide carrier, debris falls away from the surgical guide during modification and is collected within the barrier drape of the cutting attachment. This helps to contain the debris within the barrier drape and allows the user to easily dispose of this debris when the cutting attachment is detached from the production apparatus.

By providing an integrated barrier drape with a surgical guide carrier, the rotation mechanism upon which the surgical guide carrier is mounted is protected from debris from the modification of the surgical guide. Furthermore, a sterile barrier is formed between the rotation mechanism and the cutting area to prevent contaminants from falling into the sterile cutting area. In addition, the barrier drape reduces the risk of the user's hands being contaminated when loading or unloading the mouldable material carrier and/or surgical guide carrier.

Respective coding elements may be provided within each of the attachments. These coding elements indicate various properties or the type of each attachment. The production apparatus can be configured to read these coding elements and determine whether the correct attachments have been fitted to produce the required surgical guide. If it is determined that the correct attachment is not fitted, the production apparatus may disable itself, for instance by disabling the driving mechanism for the cutting attachment.

While the above described embodiments refer to drill attachments with drill bits, alternative cutting or modification means may be implemented in the cutting attachments. Appropriate alternative cutting tools include burs, knives, bores, reamers, saw blades, needles, or any other tools with appropriate cutting edge. Alternatively, a blunt tool may be utilised where the impression is still malleable. Nevertheless, the same concepts apply, in that a cutting/modification attachment is located centrally on a cutting/modification attachment that includes a barrier drape that being may be lifted around the cutting/modification area to provide a sterile barrier against contaminants.

While the above embodiments describe upper, lower, and intermediate support rings of the barrier drape of the drill attachments, these need not be circular, and may be any shape forming a loop, such as a square, rectangle, or otherwise.

While the above embodiments describe a mouldable material carrier comprising front and rear parts that are secured to each other, alternative embodiments may comprise additional parts that are bound together. Alternatively, the mouldable material carrier may be formed as a single unit, for instance, via additive manufacturing.

While the above embodiments describe how a production apparatus may register the scan of an impression of a surgical site with the anatomical features of a patient and determine how to modify the impression to produce a surgical guide, this may instead be performed by an external computer. Accordingly, the controller may be connected to the production apparatus for performing the steps. The production apparatus may be configured to transfer the scan of the impression to the controller and to receive, from the controller, instructions for modifying the impression. Equally, this controller may be integrated within the production apparatus.

The above description relates to surgical guide production apparatuses and attachments for surgical guide production apparatuses. Having said this, further embodiments are not limited to this use, and are configured for use in shaping bone to produce a bone graft for use in surgery. This may be in addition to, or instead of, being configured to produce a surgical guide.

Bone grafts can be utilised where additional bone needs to be added to the surgical site. For instance, when performing a total shoulder arthroplasty procedure a prosthesis is fitted within the glenoid cavity of the scapula. In cases where patients have significant glenoid wear, positioning and ensuring the prosthesis is located securely can be troublesome. In these cases a bone graft can be added to fill out the surgical site so that the prosthesis may be fitted more securely and in the desired anatomical position, whilst also preserving bone in the surgical site.

Bone grafts are often sourced from bone taken from the patient. This is particularly the case in total shoulder arthroplasty where the bone can be easily taken from the portions of the humerus (e.g. the humeral head) that are cut away and replaced with prosthesis. The removed bone (which would otherwise be discarded) can be formed into a bone graft for the surgical site.

The production apparatus described herein can be utilised to shape bone into a bone graft. During the preoperative phase, the shape of the required bone graft can be determined from scans of the patient (e.g. CT scans). This shape can include guide holes (or other forms of registration portions) for aligning the bone graft correctly within the surgical site. This can make use of the guiding elements (e.g. pins) provided via a surgical guide produced by the production apparatus.

To produce the bone graft the donor bone can be mounted within the production apparatus. In one embodiment, the bone is mounted on the mounting point. This may be achieved via a carrier that is configured to hold the bone and be mounted to the mounting point. The bone may be secured to the mounting point/carrier via a vice, screws, etc. Alternatively, the bone may be mounted to the surgical guide described herein (or a 3D printed sterile guide) that, in turn, is mounted to the surgical guide carrier.

Once mounted on the mounting point, the production apparatus is configured to scan the surface of the bone to register the shape of the bone and determine where to cut the bone. A cutting element such as a burr or mill is provided for cutting away the bone. The production apparatus is configured to shape the bone into the bone graft using the cutting element. This effectively forms a 5-axis milling machine (including the X, Y, Z, tilt and yaw axes described with reference to FIG. 1).

As only one side of the bone may be modified at a time, the bone may be removed from the production apparatus, flipped, and remounted to allow the modification of both sides of the bone to shape the whole of the bone graft. Alternatively, only one side may be shaped by the production apparatus and the other side may be shaped by the surgeon when the bone graft is fitted.

The production apparatus may include multiple different cutting elements for use in modifying the bone. For instance, a mill, bur, drill and/or saw may be used to shape the bone. The various cutting elements may be mounted within the production apparatus and the production apparatus may be configured to change between cutting elements as required. For instance, the coupling section for the cutting element may deposit within the mount a cutting element that is initially secured within the coupling section and retrieve a new cutting element for use in cutting the bone. Naturally, this mechanism may also be used when modifying a mould to produce a surgical guide.

The bone graft may be shaped to fit within the surgical site. To achieve this more accurately, a mould of the surgical site may be taken and used to determine the correct shape for the bone graft. The mould may be scanned by the production apparatus to determine the shape of the surgical site. Where a surgical guide is also being formed, the same mould may be used for both purposes (i.e. for producing the surgical guide and for determining the required shape of the bone graft).

The bone graft may be shaped to fit over guiding elements fixed within the surgical site such as guide pins/rods. Alternatively, or in addition, the bone graft may be shaped to fit within a corresponding recess formed within the surgical site. For instance, a recess may be cut into the bone within the surgical site into which the bone graft may be fitted (using the mould described above). By fitting the bone graft within a recess, movement of the bone graft within the surgical site can be reduced.

In light of the above, production apparatus according to embodiments described herein may be configured to modify bone to produce a bone graft. These embodiments may or may not make use of the attachments described herein that include integrated barrier drapes. Where the integrated barrier drape attachments are utilised, these attachments may be modified for use producing bone grafts. For instance, the surgical guide carrier can be a bone carrier for mounting the donor bone to the production apparatus. Equally, the cutting attachment may be modified to include alternative cutting elements (such as a mill or burr) or to include replaceable cutting elements.

While certain arrangements have been described, the arrangements have been presented by way of example only, and are not intended to limit the scope of the inventions. Indeed, the novel methods and devices described herein may be embodied in a variety of other forms; furthermore, various omissions, substitutions and changes in the form of the methods and systems described herein may be made.

What is claimed is:

1. A cutting attachment for use on a surgical guide production apparatus, the cutting attachment comprising:
a cutting element;
a connector for connecting the cutting element to a drive mechanism of the surgical guide production apparatus so that the cutting element can be driven by the drive mechanism to modify an impression of a surgical site to produce a surgical guide; and
a protective barrier comprising a flexible sheet and configured to be positioned around the cutting element to surround a cutting area to help prevent contaminants from entering or leaving the cutting area during modification of the impression; and
a support assembly comprising:
a lower support, and
an upper support separate from the lower support, wherein the protective barrier is coupled to the lower support and the upper support, and wherein a radial portion of the flexible sheet extends radially outwards from the cutting element towards the lower support such that the cutting element is radially movable relative to at least the lower support.

2. The cutting attachment of claim 1, wherein the support assembly is configured to be moved to position the protective barrier around the cutting area.

3. The cutting attachment of claim 2, wherein the support assembly is configured to couple to a driven support arm of the surgical production apparatus so that the surgical production apparatus can move the protective barrier into position around the cutting area.

4. The cutting attachment of claim 1, further comprising one or more support frames connected to the protective barrier and configured to be positioned around the cutting area to prevent the protective barrier from entering the cutting area.

5. The cutting attachment of claim 1, wherein the cutting element comprises a cutting element for a power tool.

6. The cutting attachment of claim 1, wherein the cutting attachment is sterile or configured to be sterilised.

7. The cutting attachment of claim 1, further comprising a coding element indicating a type of the cutting attachment and configured to be read by the surgical guide production apparatus so that the surgical guide production apparatus can verify that the correct type of cutting attachment has been fitted.

8. The cutting attachment of claim 1, wherein an inner end of the radial portion is coupled to the connector, an outer end of the radial portion is coupled to the lower support, and the connector and the lower support are radially movable relative to each other independently from the upper support.

* * * * *